(12) United States Patent
Sanchez et al.

(10) Patent No.: US 11,730,410 B2
(45) Date of Patent: Aug. 22, 2023

(54) NEEDLE IMPEDANCE ELECTROMYOGRAPHY AND ELECTRICAL IMPEDANCE IMAGING FOR ENHANCED MUSCLE DIAGNOSTICS

(71) Applicant: Beth Israel Deaconess Medical Center, Inc., Boston, MA (US)

(72) Inventors: Benjamin Sanchez, Brookline, MA (US); Seward B. Rutkove, Brookline, MA (US); Hyeuknam Kwon, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 732 days.

(21) Appl. No.: 16/613,609

(22) PCT Filed: May 16, 2018

(86) PCT No.: PCT/US2018/033032
§ 371 (c)(1),
(2) Date: Nov. 14, 2019

(87) PCT Pub. No.: WO2018/213495
PCT Pub. Date: Nov. 22, 2018

(65) Prior Publication Data
US 2020/0297235 A1 Sep. 24, 2020

Related U.S. Application Data

(60) Provisional application No. 62/506,784, filed on May 16, 2017.

(51) Int. Cl.
*A61B 5/296* (2021.01)
*A61B 5/0536* (2021.01)
(Continued)

(52) U.S. Cl.
CPC ............ *A61B 5/296* (2021.01); *A61B 5/0536* (2013.01); *A61B 5/0538* (2013.01); *A61B 5/262* (2021.01); *A61B 5/6848* (2013.01)

(58) Field of Classification Search
CPC ..... A61B 5/296; A61B 5/0536; A61B 5/0538; A61B 5/6848; A61B 5/389; A61B 5/4519; A61B 2562/02
See application file for complete search history.

(56) References Cited

U.S. PATENT DOCUMENTS

| 5,575,292 A | 11/1996 | Brown et al. |
| 9,014,797 B2 | 4/2015 | Shiffman et al. |

(Continued)

FOREIGN PATENT DOCUMENTS

| CN | 103479354 A | 1/2014 |
| CN | 103815903 A | 5/2014 |

(Continued)

OTHER PUBLICATIONS

Invitation to Pay Additional Fees for International Application No. PCT/US2018/033032, dated Jul. 3, 2018.
(Continued)

*Primary Examiner* — David J. McCrosky
*Assistant Examiner* — Nidhi N Patel
(74) *Attorney, Agent, or Firm* — Wolf, Greenfield & Sacks, P.C.

(57) ABSTRACT

Described herein are embodiments of methods and apparatus for diagnosing neuromuscular diseases using an impedance-EMG needle, and for generating electrical impedance images using an impedance needle. Some embodiments provide an apparatus including an impedance-EMG needle, including both EMG electrodes and impedance electrodes, to measure both active and passive electrical properties of muscle. Other embodiments provide an apparatus including
(Continued)

an impedance needle, including a plurality of impedance electrodes to measure impedance in tissue surrounding the impedance needle to generate an electrical impedance image. Use of such methods and apparatus may be advantageous in improving the accuracy of assessing and diagnosing neuromuscular disease.

19 Claims, 14 Drawing Sheets

(51) Int. Cl.
    *A61B 5/0538*     (2021.01)
    *A61B 5/00*     (2006.01)
    *A61B 5/262*     (2021.01)

(56) References Cited

U.S. PATENT DOCUMENTS

| | | |
|---|---|---|
| 9,974,463 B2 | 5/2018 | Rutkove et al. |
| 10,898,100 B2 | 1/2021 | Rutkove et al. |
| 10,973,431 B2 | 4/2021 | Rutkove et al. |
| 2002/0123674 A1 | 9/2002 | Plichi et al. |
| 2004/0082978 A1 | 4/2004 | Harrison et al. |
| 2005/0075629 A1 | 4/2005 | Chapelon et al. |
| 2006/0276702 A1 | 12/2006 | McGinnis |
| 2008/0177398 A1* | 7/2008 | Gross ............... A61B 5/205 700/11 |
| 2009/0088608 A1 | 4/2009 | Mumford et al. |
| 2010/0292603 A1* | 11/2010 | Shiffman ............ A61B 5/053 600/547 |
| 2012/0245436 A1 | 9/2012 | Rutkove et al. |
| 2012/0323136 A1 | 12/2012 | Shiffman et al. |
| 2013/0237795 A1 | 9/2013 | Carr |
| 2015/0196220 A1 | 7/2015 | Rutkove et al. |
| 2015/0216442 A1 | 8/2015 | Lavy et al. |
| 2016/0081585 A1 | 3/2016 | Halter |
| 2016/0242661 A1 | 8/2016 | Fischell et al. |
| 2016/0341684 A1 | 11/2016 | Choi |
| 2017/0007151 A1 | 1/2017 | Rutkove et al. |
| 2019/0069801 A1 | 3/2019 | Rutkove et al. |
| 2021/0361185 A1 | 11/2021 | Rutkove et al. |

FOREIGN PATENT DOCUMENTS

| | | |
|---|---|---|
| FR | 2 985 418 A1 | 7/2013 |
| JP | H02-189129 A | 7/1990 |
| JP | H11-502442 A | 3/1999 |
| JP | 2004-081234 A | 3/2004 |
| JP | 2011-507648 A | 3/2011 |
| WO | WO 2017/066734 A1 | 4/2017 |

OTHER PUBLICATIONS

International Search Report and Written Opinion for International Application No. PCT/US2018/033032, dated Sep. 7, 2018.
International Preliminary Report on Patentability for International Application No. PCT/US2018/033032, dated Nov. 28, 2019.
U.S. Appl. No. 11/992,430, filed Aug. 3, 2010, Rutkove, Seward B.; Shiffman, Carl A.; Aaron, Ronald.
U.S. Appl. No. 13/598,109, filed Aug. 29, 2012, Rutkove, Seward B.; Shiffman, Carl A.; Aaron, Ronald.
U.S. Appl. No. 14/660,855, filed Mar. 17, 2015, Rutkove, Seward B.; Shiffman, Carl A.; Aaron, Ronald.
U.S. Appl. No. 13/391,484, filed Jun. 6, 2012, Rutkove, Seward B.; Dawson, Joel L.
U.S. Appl. No. 15/961,714, filed Apr. 24, 2018, Rutkove, Seward B.; Dawson, Joel L.
U.S. Appl. No. 15/117,929, filed Aug. 10, 2016, Rutkove, Seward B.; Terrones, Benjamin Sanchez.
U.S. Appl. No. 16/613,609, filed Nov. 14, 2019, Sanchez, Bejnamin; Rutkove, Seward B.; Kwon Hyeuknam.
Extended European Search Report dated Feb. 8, 2021 in connection with European Application No. 18802378.2.

* cited by examiner

NEEDLE IMPEDANCE ELECTROMYOGRAPHY AND ELECTRICAL IMPEDANCE IMAGING FOR ENHANCED MUSCLE DIAGNOSTICS

RELATED APPLICATIONS

This Application is a national stage filing under 35 U.S.C. § 371 of International Patent Application Serial No. PCT/US2018/033032, filed May 16, 2018, which claims priority to U.S. Provisional Application Ser. No. 62/506,784, filed on May 16, 2017, the contents of which are incorporated herein by reference in their entirety.

FEDERALLY SPONSORED RESEARCH

This invention was made with government support under grant R01 NS091159 awarded by NIH. The government has certain rights in the invention.

BACKGROUND

Weakness, disability, and death can be significant clinical consequences of neuromuscular disorders (NMD). Although there have been inroads in the treatment of such diseases, a number still remain without effective therapy.

Needle electromyography (EMG) is the standard office-based test and principal clinical tool to assess NMD. Over one million EMG studies are performed annually in the United States for assessment of patients suffering from a variety of conditions, including nerve root compression, amyotrophic lateral sclerosis, and myopathy.

SUMMARY

In another embodiment, there is provided an impedance-EMG needle configured to be inserted into tissue, the impedance-EMG needle comprising: a shaft; at least one EMG electrode, disposed on the shaft, configured to measure active electrical properties of the tissue; and a plurality of impedance electrodes, disposed on the shaft, configured to measure passive electrical properties of the tissue. In some embodiments, the active electrical properties comprise depolarization of muscle fiber membrane.

In another embodiment, there is provided a system for assessing neuromuscular disease of tissue, the system comprising: an impedance-EMG needle configured to be inserted into tissue, the impedance-EMG needle comprising: a shaft; at least one EMG electrode, disposed on the shaft, configured to measure active electrical properties of the tissue; and a plurality of impedance electrodes, disposed on the shaft, configured to measure passive electrical properties of the tissue; and at least one computing device configured to receive and analyze at least one signal from the impedance-EMG needle.

In another embodiment, there is provided a method for assessing neuromuscular disease of tissue, the method comprising: inserting an impedance-EMG needle into the tissue, the impedance-EMG needle comprising: a shaft; at least one EMG electrode, disposed on the shaft, configured to measure active electrical properties of the tissue; and a plurality of impedance electrodes, disposed on the shaft, configured to measure passive electrical properties of the tissue; and determining, from the active electrical properties and the passive electrical properties, a state of the tissue.

In another embodiment, there is provided an impedance needle configured to be inserted into tissue, the impedance needle comprising: a shaft; and a plurality of impedance electrodes, disposed on the shaft, configured to measure passive electrical properties of the tissue.

In another embodiment, there is provided a system configured to assess tissue, the system comprising: an impedance needle configured to be inserted into tissue, the impedance needle comprising: a shaft; and a plurality of impedance electrodes, disposed on the shaft, configured to measure passive electrical properties of the tissue; and at least one computing device configured to receive and analyze at least one signal from the impedance-EMG needle.

In another embodiment, there is provided a method for generating an impedance image of tissue, the method comprising: inserting an impedance needle into the tissue, the impedance needle comprising: a shaft; and a plurality of impedance electrodes, disposed on the shaft, configured to measure passive electrical properties of a volume of tissue surrounding the plurality of impedance electrodes; and reconstructing the impedance image from the passive electrical properties of the tissue measured by the plurality of impedance electrodes.

In another embodiment, there is provided a method for assessing tissue, the method comprising: inserting at least one impedance needle into the tissue, each of the at least one impedance needles comprising: a shaft; and a plurality of impedance electrodes, disposed on the shaft, configured to measure passive electrical properties of the tissue; and determining a state of the tissue from the passive electrical properties measured by the at least one impedance needle.

DETAILED DESCRIPTION

Figure 1:
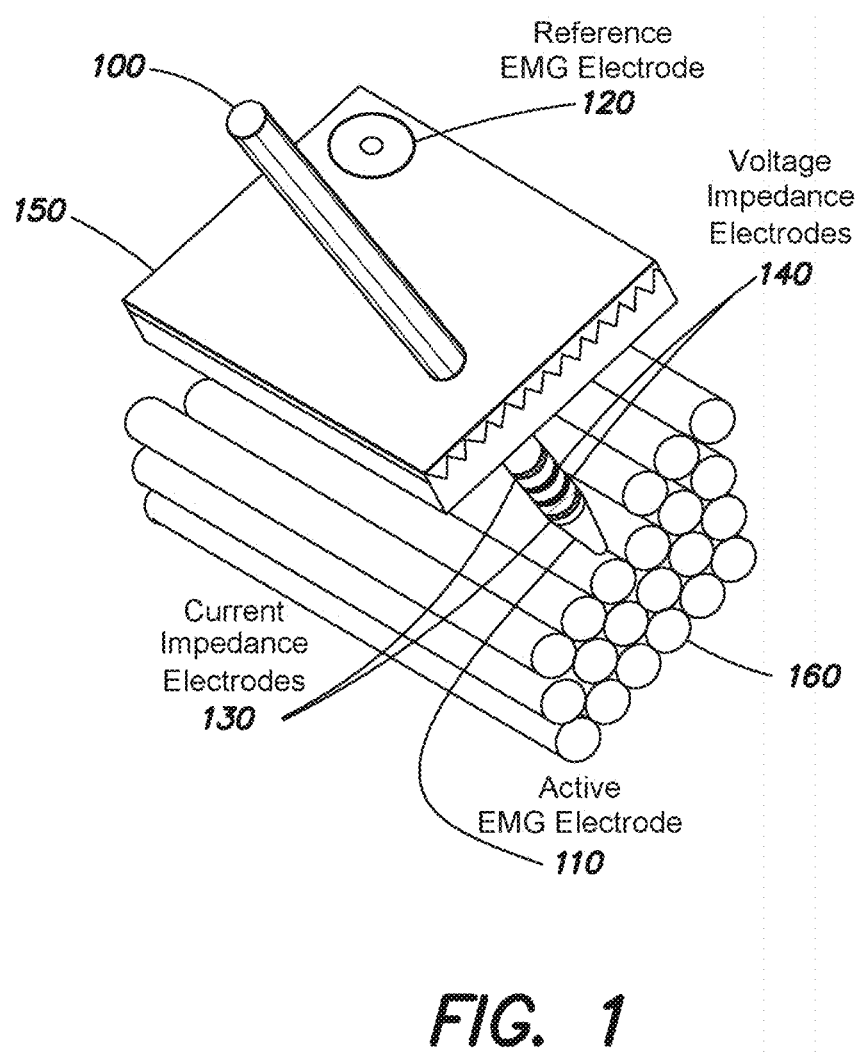
FIG. 1 illustrates an embodiment of the impedance-EMG needle while inserted into tissue.

In needle EMG, a needle is inserted through a patient's skin and subcutaneous fat into a muscle of interest using anatomical landmarks. Once placed in the muscle, the needle is gently maneuvered through the tissue to intentionally irritate and injure individual myocyte membranes. With each passage of the needle, electrical discharges are measured from the resulting membrane depolarization. The physician seeks to identify abnormal spontaneous potentials, including repetitive discharges from a single muscle fiber (e.g. fibrillation potentials and myotonic potentials) or from groups of muscle fibers (e.g. fasciculation potentials and myokymic potentials). Once this part of the procedure is completed, the patient is asked to contract the muscle and the electrical characteristics of the voluntary motor unit potentials are evaluated as well as their recruitment patterns.

During this procedure, the physician monitors the patient to ensure that the muscle is being correctly activated while simultaneously scrutinizing the EMG signal displayed on a screen. Once the test is completed, the physician makes subjective decisions regarding the status of the muscle, grading abnormalities on a 0-3 scale for both "spontaneous activity" (the part of the exam in which the muscle is at rest) and "voluntary motor unit analysis" (the part of the exam in which the patient intentionally contracts the muscle).

EMG examination appears to have remained the standard approach to NMD assessment for a variety of reasons. These include (1) the ability to sample a variety of muscles, (2) a high sensitivity to the presence of disease, and (3) the capability of identifying the acuity/chronicity of a problem. Such advantages have made EMG the standard test used to evaluate nerve and muscle disorders.

However, there are aspects of EMG that have limited the technology. First, EMG can only assess the electrical activity of the muscle fiber membrane. While this is valuable, it says nothing about the non-electrical aspects of the tissue. Most neuromuscular diseases impact the tissue in complex ways, causing major alterations in its histology. For example, myopathies may have large numbers of inflammatory cells, edema, and fat and connective tissue deposition. Neurogenic diseases are associated with myofiber atrophy, fiber type grouping, and intracellular edema. Needle EMG is essentially "blind" to these underlying alterations, the data being based on the secondary effects of these changes on the active electrical properties of the fibers' membrane. Second, needle EMG fails to provide information on the contractile apparatus of the muscle itself, since it only measures up to the point of muscle fiber depolarization. Sarcomeric disruption, extracellular connective tissue deposition, and other abnormalities can all impact muscle force, but still leave the EMG signal unaffected. Finally, as commonly practiced, EMG is subjective with the physician rating abnormalities on a coarse 0-3 ordinal scale (normal, mild, moderate, and severe). Studies have shown repeatability difficulties even among expert electromyographers, with only 60% inter-rater agreement rates and a specificity for disease of only 70%. While quantitative EMG methods exist, they may not be used in practice given their very time consuming nature.

Recently, other technologies have also been employed in the evaluation of NMD to assist EMG in the diagnostic process. Standard metrics based on force can detect deterioration of muscle performance, however, they usually require the use of cumbersome equipment and patient cooperation, the latter difficult to achieve if there is associated pain.

Muscle edema, fatty infiltration, and mass lesion can cause abnormal signal intensity in magnetic resonance imaging (MRI) and computerized tomography. However, the use of such technologies may be costly and, perhaps more importantly, they may not be able to be employed where they are needed the most—at the bedside to help physicians while evaluating a patient face-to-face.

Ultrasound is another available imaging technology that can be used at the bedside. However, the signal quality has limited reproducibility and interpretation largely depends on the physician's expertise. To date, despite limitations, other technologies have not been able to replace EMG as the primary NMD diagnostic tool.

Electrical impedance is a fourth alternative technology for muscle evaluation that has recently been used. Impedance's main value has been to assess NMD status, although it can also provide diagnostic information, being able to discriminate myopathic from neurogenic disease. In impedance measurements, a weak, high frequency electrical current is passed between two electrodes and the resulting voltages are measured by a second set of electrodes. The basic underlying principle of impedance is that it can provide detailed data on the microscopic structure of biological tissues. Established uses of impedance in biology and medicine fields include lung tissue and other organ status characterization, monitoring of cell concentration in adherent animal cell cultures, and cell sporting in a "lab-on-a-chip." In general, impedance relies upon the concept that electrical current that is applied to a material is altered as a function of the frequency due to the inherent electrical properties of the material. A cell membrane may act as a capacitor and thus may be highly frequency dependent. In particular, when electrical current is applied to skeletal muscle and the frequency of the current signal is varied in the kHz-MHz range, the high (MHz) and low (kHz) frequency electrical current flow through the resistive extracellular ionic medium. However, due to the capacitive behavior of the fiber membrane, only the high frequency current can propagate through the intracellular medium. The frequency dependence in biological tissues can be described by using models, typically including series and parallel combinations of resistors and capacitors accounting for the variety of cell sizes and morphology. Previous studies using surface electrodes placed over the skin have shown the muscle impedance's sensitivity to tissue condition and its alteration with disease using electrodes applied to the skin. This approach has shown sensitivity to disease status in a variety of disorders.

Unlike the other technologies listed above, electrical impedance is a technique that lends itself naturally to being combined with EMG. First, impedance measures muscle's passive electrical properties, thus complementing the active electrical information provided by EMG. Second, impedance can provide quantitative data during measurements of a muscle at rest as well as during muscle contraction. Finally, and unlike some other technologies, impedance has the potential of being seamlessly integrated within the EMG needle itself, enabling simultaneous impedance and EMG recordings without affecting the complexity or duration of the EMG test.

Furthermore, combining impedance and EMG measurements may allow for the assessment of conditions that previously were not readily accessible to EMG, such as disuse muscle atrophy or atrophy induced by old age (sarcopenia). Alterations in these conditions on EMG are relatively subtle, and thus EMG is generally not considered a useful technology for their evaluation. By combining EMG and impedance, it may be possible to obtain data that would allow for these conditions to be diagnosed and quantified.

Additionally, assessment of exercise-induced alterations, including muscle fatigue or overuse, may be possible with the combination of EMG and impedance measurements. Again, EMG abnormalities in these situations may be subtle, but impedance alterations may be substantial. Combining the technologies may provide valuable additional information to quantify exercise-related effects.

The inventors have recognized and appreciated the need for an approach for more accurately diagnosing patients with NMD and assessing severity. Described herein are embodiments of an approach that uses an impedance-EMG needle for human use to co-register and co-localize simultaneous impedance and EMG data intramuscular recordings. The new needle may allow physicians to obtain a complete electrical characterization of muscle by detecting concomitant alterations in muscle's active (EMG) and passive (impedance) electrical properties at the same measurement site.

FIG. 1 illustrates an embodiment of the impedance-EMG needle while inserted into a patient, through skin 150 and into tissue 160. The needle may include a shaft 100 which may include multiple electrodes in order to record both EMG and impedance data. The needle may include an active EMG electrode 110, which may be located at the distal end of the shaft 100. There may also be a reference EMG electrode 120, which may be located on the skin 150. In moving through the tissue 160, the active EMG electrode 110 and the reference EMG electrode 120 may measure active electrical properties of the tissue, such as depolarization of muscle fibers. The tip of the needle may be sharped or beveled or any other shape so as to penetrate the tissue easily and access muscle.

The needle may also include current impedance electrodes 130 and voltage impedance electrodes 140. As shown, the current impedance electrodes 130 and voltage impedance electrodes 140 may be configured as rings around the shaft 100 of the needle. The device may drive a current through the current impedance electrodes 130, while measuring corresponding voltages through the voltage impedance electrodes 140. In doing so, the current impedance electrodes 130 and voltage impedance electrodes 140 may measure passive electrical properties of the tissue, such as resistance and reactance. In some embodiments, the current impedance electrodes 130 and voltage impedance electrodes 140 may measure passive electrical properties at different angles with respect to the direction of muscle fibers.

In some embodiments, the impedance-EMU needle (e.g., the impedance-EMG needle described in connection with FIG. 1) may be configured to measure EIM and EMG while a muscle is at rest and while the muscle is contracted. A clinician may insert the impedance-EMG needle into a muscle of a patient, and ask the patient to rest the muscle. While the muscle is at rest, the impedance-EMG needle may be configured to measure active electrical properties (with the EMG electrodes) as well as passive electrical properties (with the impedance electrodes). Once this part of the procedure is complete, the patient may be instructed to contract the muscle. While the muscle is contracted, the impedance-EMG needle may be configured to measure active electrical properties (with the EMG electrodes) as well as passive electrical properties (with the impedance electrodes).

Both EMG and EIM measurements may change when the muscle is contracted compared with when the muscle is at rest. Various nerve and muscle diseases, as well as injury, and disuse, may change the active electrical properties and the passive electrical properties of muscle in different ways when the muscle is at rest and when the muscle is contracted. By measuring both active and passive electrical properties during both states of the muscle, the impedance-EMG needle may be able to more accurately assess the muscle and diagnose problems in the muscle.

The shaft 100 of the needle may have a length such that EMG measurements and impedance measurements may be obtained from a desired location of tissue. For example, if a physician wishes to obtain EMG measurements and impedance measurements from a patient's thigh, the shaft 100 of the needle may have a longer length than if the physician wished to obtain EMG measurements and impedance measurements from the patient's finger.

As discussed, the clinical application of impedance for diagnosing patients with NMD has thus far been to use surface electrodes placed over the muscle of interest. Unlike surface-based impedance approaches, the needle thus described may be able to record impedance directly in the muscle at the same measurement site as the EMG simultaneously. The integration of impedance and EMG technology may have numerous benefits.

First, impedance-EMG technology may provide muscle impedance data of deep muscles. Existing surface impedance approaches to evaluate muscle health using wet or dry electrodes placed in contact with the skin are convenient to use because they are easy to apply. However, surface impedance data are impacted by skin moisture and subcutaneous fat thickness. As a result, the sensitivity to detect changes occurring in deep muscle beds is limited. Impedance-EMG technology may overcome this limitation and enable accurate assessment not only in superficial but also deep muscles. Impedance-EMG technology may also be valuable in assessing individuals who are obese.

Second, impedance-EMG technology may allow greater impedance spatial specificity. Surface impedance methods are limited at detecting global alterations in the "bulk" electrical properties of skin, subcutaneous fat and muscle tissues. In many neuromuscular conditions, however, the disease impacts the muscle heterogeneously, for example inflammatory myopathies. With impedance-EMG technology, it may be possible to evaluate the impedance of the muscle at the point of the electrode contact where the EMG is measured with a spatial specificity of less than 1 $cm^3$.

Third, impedance-EMG technology may provide muscle biopsy-like data in vivo. The impedance-EMG technology may have the ability to provide quantitative muscle biopsy-type data (e.g. muscle fiber size and amount of connective tissue) in a straightforward manner to the physician, without increasing the complexity or duration of the EMG test.

Figure 2A:
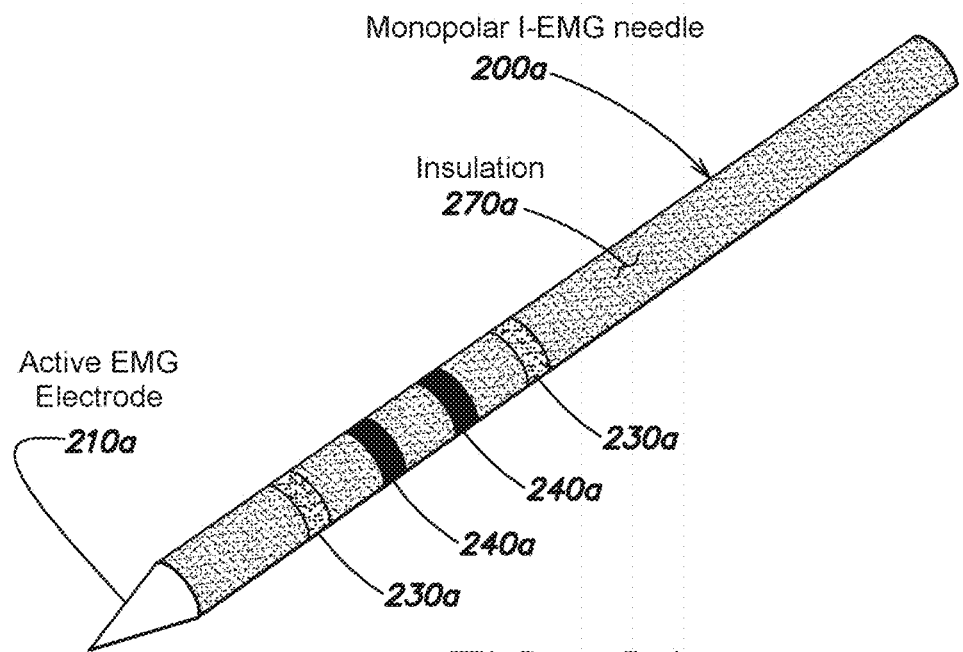
FIG. 2A illustrates an embodiment in which the impedance-EMG needle includes a monopolar EMG design.
Figure 2B:
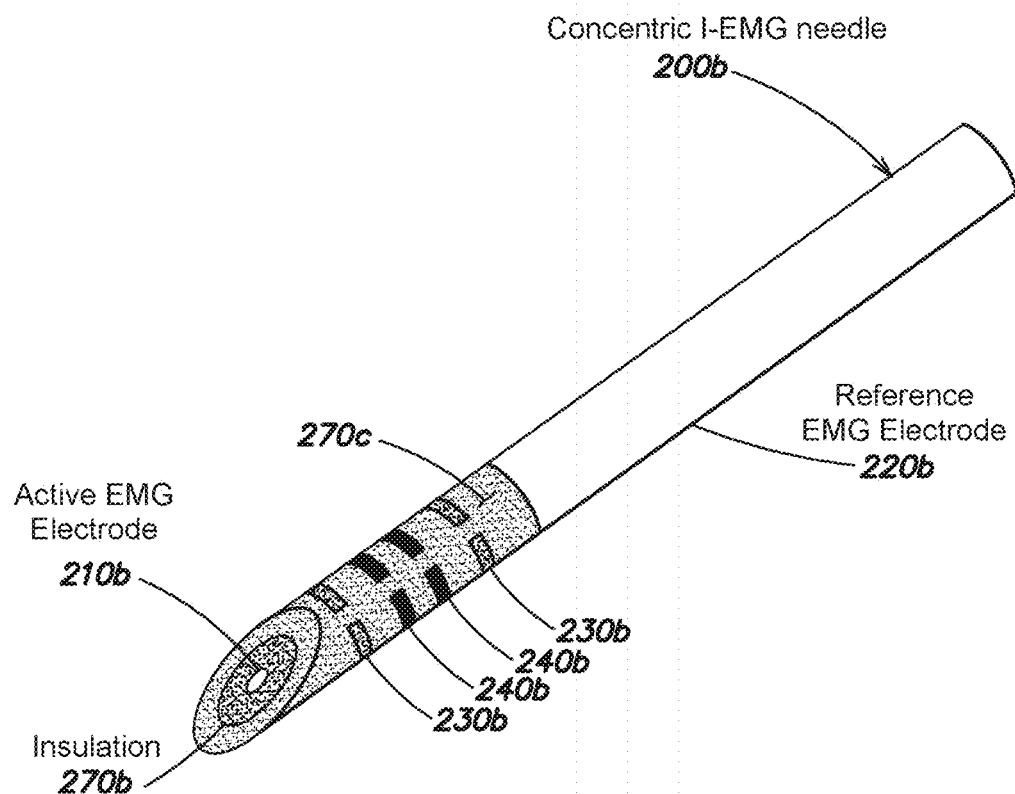
FIG. 2B illustrates an embodiment in which the impedance-EMG needle includes a concentric EMG design.

In some embodiments, the impedance-EMG needle may include a monopolar EMG design. In other embodiments, the impedance EMG needle may include a concentric EMG design. FIG. 2A illustrates an embodiment in which the impedance-EMG needle includes a monopolar EMG design, and FIG. 2B illustrates an embodiment in which the impedance-EMG needle includes a concentric EMG design.

In the embodiment in which the impedance-EMG needle includes a monopolar EMG design, the needle may include a shaft 200a with insulation 270a on the outer layer of the shaft 200a. Similar to FIG. 1, the needle may include an active EMG electrode 210a on the distal end of the shaft, and a reference EMG electrode may be located on the skin of the patient. The needle may also include current impedance electrodes 230a and voltage impedance electrodes 240a.

In the embodiment in which the impedance-EMG needle includes a concentric EMG design, the needle may include a shaft 200b with a reference EMG electrode 220b on the outer layer of the shaft 200b. The shaft 200b may include an insulation layer 270b on the inside of the reference EMG electrode 220b, and an active EMG electrode 210b on the inside of the insulation layer 270b. The needle may also include current impedance electrodes 230b and voltage impedance electrodes 240b. In some embodiments, the reference EMG electrode 210b may not extend to the tip of impedance-EMG needle. In such an embodiment, the reference EMG electrode 210b may only extend to a portion of the shaft 200b just before the current impedance electrodes 230b and the voltage impedance electrodes 240b. For example, the reference EMG electrode 210b may only extend to a portion of the shaft 200b before the current impedance electrode 230b that is further from the distal end of the shaft 200b. In such an embodiment, there may include additional insulation 270c that begins at the point the reference EMG electrode 210b extends to, and the current impedance electrodes 230b and the voltage impedance electrodes 240b may be disposed on this additional insulation 270c.

In other embodiments, the reference EMG electrode 220b may extend to the distal end of the shaft 200b. In such an embodiment, there may be insulation (e.g., rings of insulation) on the reference EMG electrode 220b on which the current impedance electrodes 230b and the voltage impedance electrodes 220b are disposed.

Figure 3:
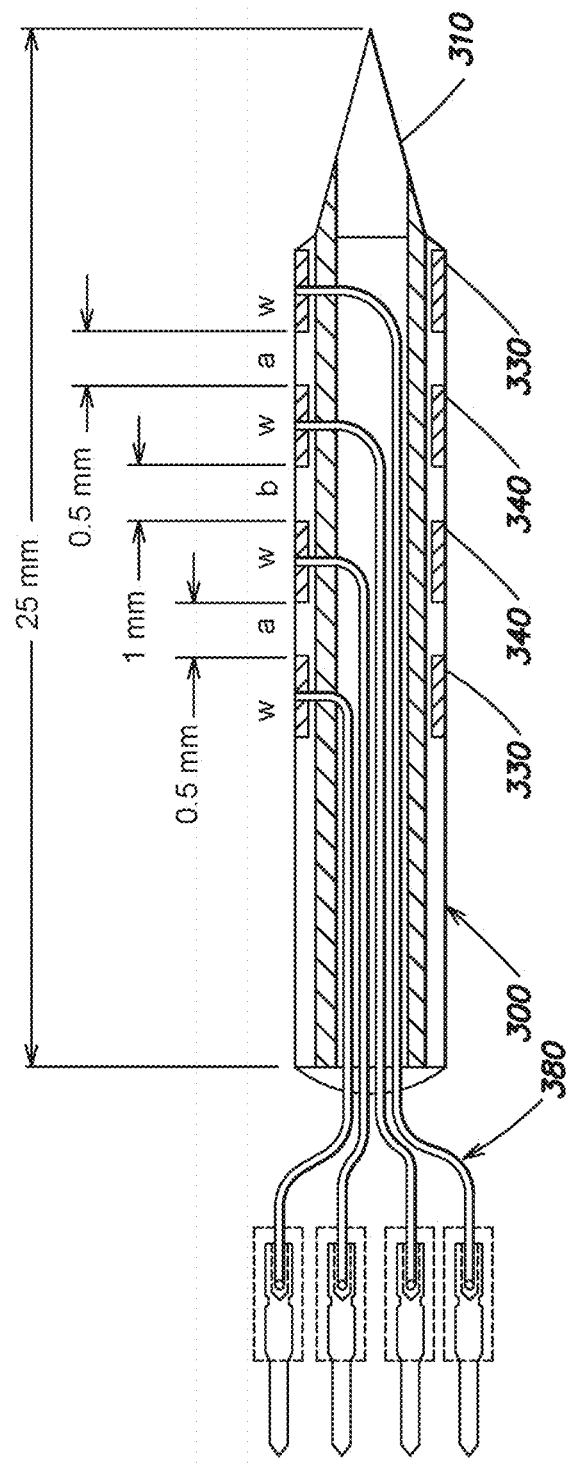
FIG. 3 illustrates a cross-sectional view of another embodiment of the impedance-EMG needle.

FIG. 3 illustrates a cross-sectional view of another embodiment of the impedance-EMG needle. In this embodiment, the impedance-EMG needle may include a shaft 300, an active EMG electrode 310, current impedance electrodes 330, and voltage impedance electrodes 340. The needle may also include wires 380 that connect the current impedance electrodes 330 and voltage impedance electrodes 340 to an external computing device, for example, a computer. The external computing device may generate, receive, and analyze signals from the current impedance electrodes 330 and voltage impedance electrodes 340. The external computing device may also receive and analyze signals relating to EMG measurements. This may be accomplished with an additional wire 380 that may connect the active EMG electrode 310 to the external computing device. There may additionally be a reference EMG electrode placed on a patient's skin, for example, and the reference EMG electrode may also be connected (e.g., with another wire 380) to the external computing device.

The spacing and size of the current impedance electrodes 330 and voltage impedance electrodes 340 may be designed to optimize the quality of the signals received from both the impedance measuring portion of the needle and the EMG measuring portion of the needle. The impedance electrodes may be designed such that the impedance measurements do not affect the EMG measurements, and the EMG measurements do not affect the impedance measurements. The impedance electrodes may also be designed such that both the EMG measurements and the impedance measurements are being obtained from the same tissue location.

The design of the impedance-EMG needle may be optimized using finite element method (FEM) simulations. First, initial design specifications may be adjusted based on preliminary experimental data for EMG electrodes. Then, the stability of the EMG active electrode may be confirmed with the addition of impedance electrodes. Different impedance electrodes' electrical and mechanical characteristics may be simulated with a 3-dimensional FEM model using numerical software (e.g. Comsol® software) based on standard designs of monopolar and concentric EMG needles including additional impedance electrodes inserted into muscle tissue. Simulations may be performed in the bandwidth from 1 Hz up to 10 MHz where impedance-EMG data may be measured, using reference permittivity tissue properties. The measurement of muscle's anisotropic properties may also be studied simulating an impedance-EMG needle with sixteen impedance electrodes distributed axially along the needle's shaft following an octagonal pattern.

In order to further optimize the design of the impedance-EMG needle, stable reproducible impedance measurements may be conducted in saline tanks and agar phantoms. The phantom conductivity may be chosen to match muscle properties at 50 kHz and measured in the range 1 kHz to 10 MHz used in simulations performed with the FEM model. The agar phantom may be made of a solution of agar in distilled water with sodium chloride. The ability of the impedance-EMG needle to measure anisotropic properties of myofibers' membranes may be tested using an approach of including inner insulating (dielectric) film layers with different thicknesses in the phantom. The needle may be inserted into the phantom to different depths. Agar-needle electrode interface impedance may be evaluated within 6 hours to ensure time-stability of the phantom.

Recording characteristics of the impedance-EMG may be tested with the needle electrodes immersed in an ungrounded saline bath and held by a grounded micromanipulator using an oscilloscope. Reference waveforms from a function generator may then be applied to a reference electrode immersed in the bath. The signal may be recorded directly from the generator using the EMG electrodes using an oscilloscope. Robustness to line interference (50/60 Hz) may be measured similarly with a grounded and ungrounded subject holding the needle and the electrical equipment in the vicinity turned on and off.

Capacitance of the impedance-EMG needle may be measured in air. The needle may then be immersed into 0.9% saline solution at room temperature. Different amplitude voltages may be applied to determine the resistance and linearity of the electrodes across various frequencies. Resistance and capacitance may be recorded multiple times after ensuring electrode stabilization. Broadband baseline noise peak and power may be measured with the needle immersed in a grounded saline bath. Total harmonic distortion may be determined summing the power of all harmonic components to the power of the fundamental frequency generated. Common-mode conversion may be tested with the needle electrode held in the ungrounded bath by the grounded micromanipulator applying bi-phasic waveforms to the reference electrode immersed in the bath.

The distance between each current impedance electrode 330 and the adjacent voltage impedance electrode 340 may have a value of a, which may be 0.5 mm. The gap between the two voltage impedance electrodes 340 may have a value of b, and may be twice the value of a, and may be 1.0 mm. Additionally, each of the current impedance electrodes 330 and the voltage impedance electrodes 340 may all have the same width w, which may be 1.0 mm. The diameter of the needle may be less than 1 mm. The shaft 300 of the impedance-EMG needle may have a length ranging from 25 mm to 40 mm, and may range from gauge 16G to 29G. The impedance electrodes contact may be less than 1 kΩ at 10 Hz and the volume resolution sensed lower than 1 $cm^3$.

In some embodiments, electrodes may be coated (e.g. via sputtering) in order to increase effective electrode area and reduce contact impedance. The sputtering process may be carried out by e-beam or physical vapor methods.

Figure 4:
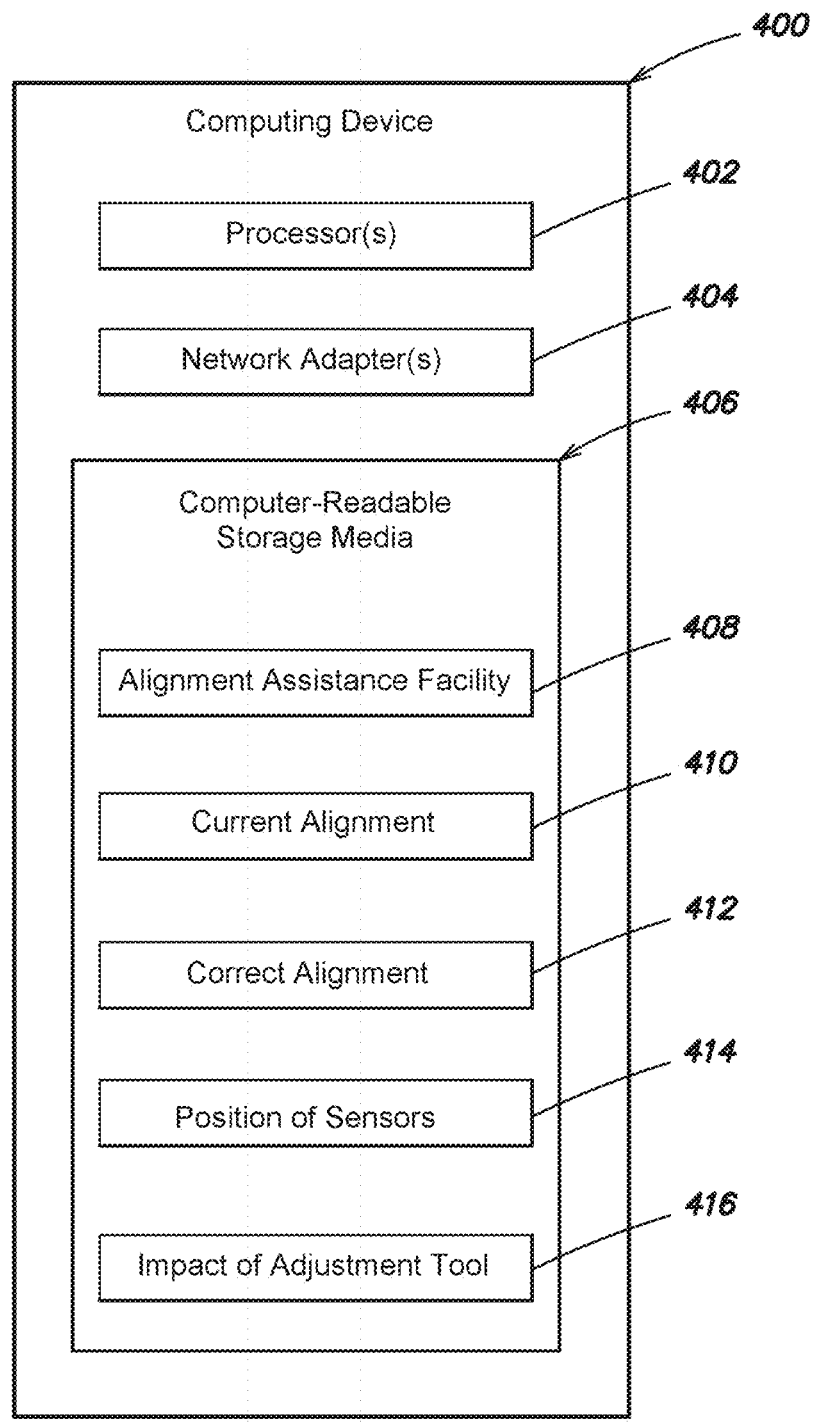
FIG. 4 illustrates an embodiment of the external computing device for receiving and processing signals from the impedance-EMG needle.

FIG. 4 illustrates an embodiment of an external computing device for receiving and analyzing signals from the impedance-EMG needle. In one embodiment, the computing device 400 may include at least one processor(s) 402 and at least one network adapter(s) 404. The computing device may also include computer readable storage media 406 which may include an alignment assistance facility module 408, a current alignment module 410, a correct alignment module 412, a position of sensors module 414, and an impact of adjustment tool module 416. The computing device 400 may be designed to receive and analyze signals from the impedance-EMG needle in order to assess and diagnose neuromuscular disease.

The computing device 400 may be designed such that it may receive and analyze signals from both the EMG measuring portion of the needle and the impedance measuring portion of the needle. The computing device 400 may analyze both signals simultaneously to obtain results that reflect both active electrical properties and passive electrical properties of the tissue being measured. The computing device 400 may display the results on a screen for a physician to analyze during operation of the impedance-EMG needle in assessing NMD of a patient.

Figure 5:
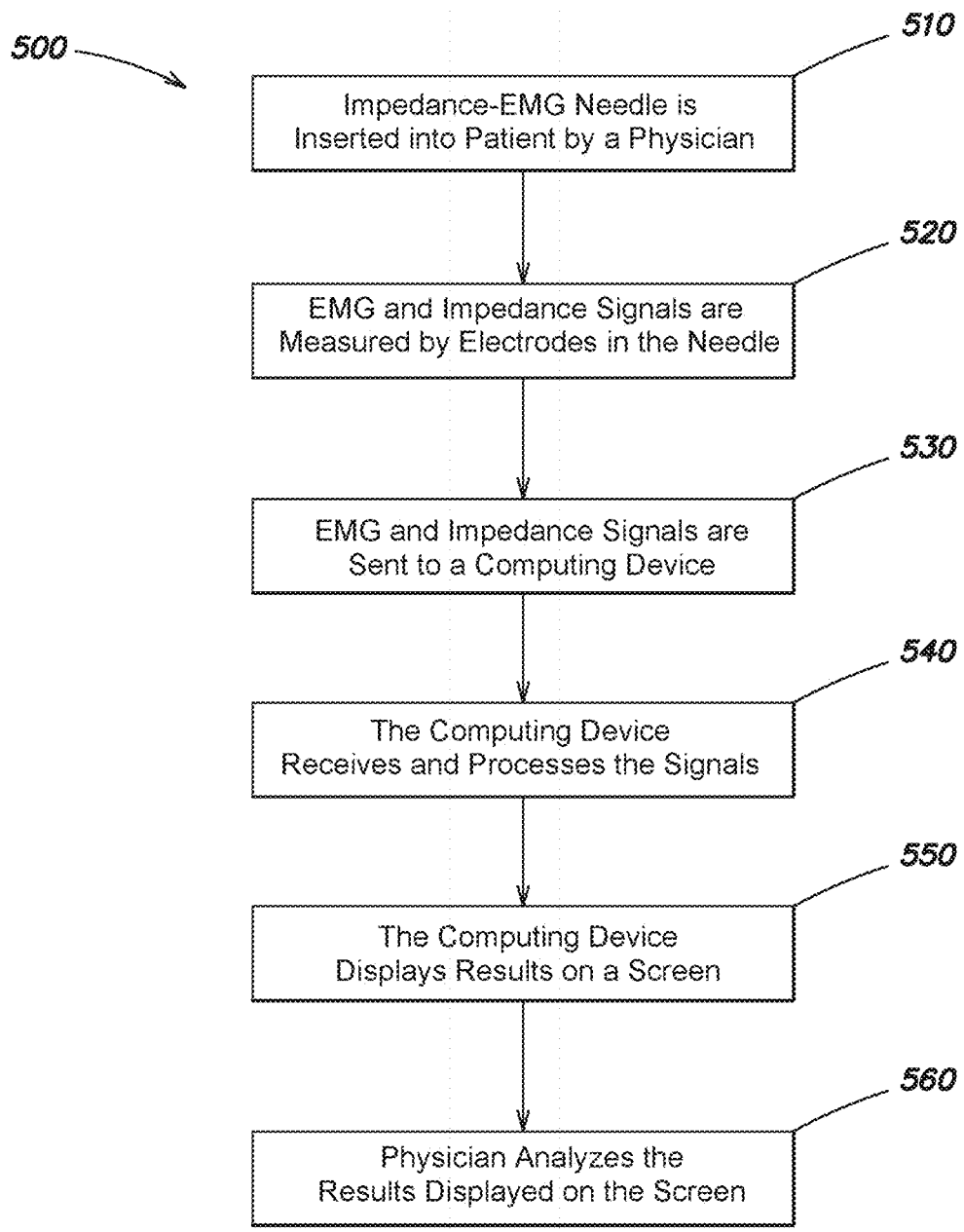
FIG. 5 is a flow chart of an example process for operation of the impedance-EMG needle.

FIG. 5 is a flow chart of an example process 500 for operation of the impedance-EMG needle. At step 510, the impedance-EMG needle may be inserted into a patient by a physician. At step 520, the impedance-EMG needle may measure both EMG and impedance signals. At step 530, the EMG and impedance signals may be sent to a computing device, for example the computing device 400 of FIG. 4. At step 540, the computing device may receive and process the EMG and impedance signals. At step 550, the computing device may display on a screen results from processing the EMG and impedance signals. At step 560, the physician may analyze the results displayed on the screen to assess and diagnose the patient's NMD.

Figure 6:
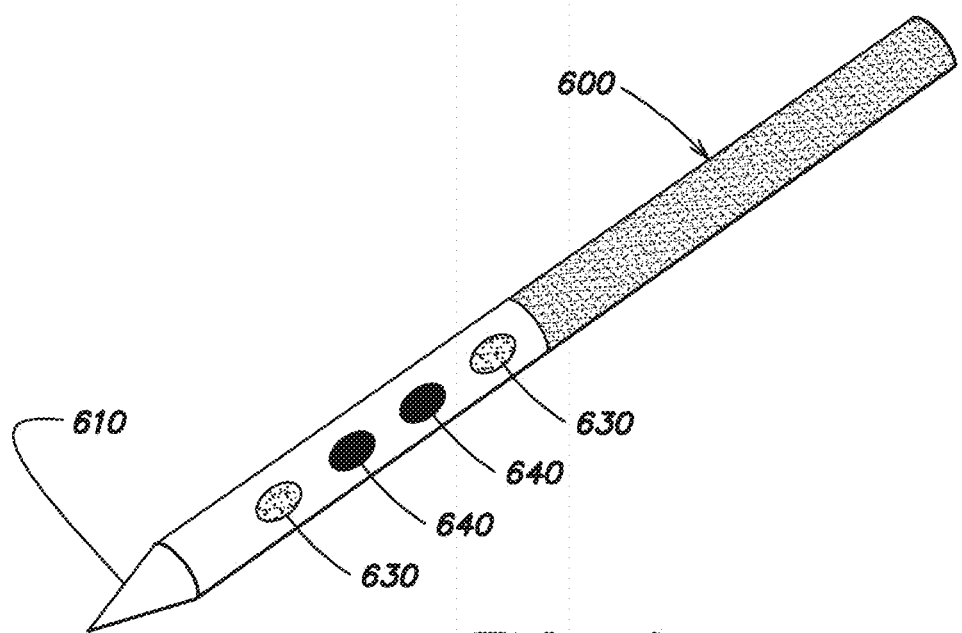
FIG. 6 illustrates an embodiment in which the impedance electrodes are point electrodes on a face of the impedance-EMG needle.

FIG. 6 illustrates an embodiment in which the current impedance electrodes 630 and voltage impedance electrodes 640 are designed as point electrodes on a face of the impedance-EMG needle, rather than rings around the needle. In such an embodiment, the current impedance electrodes 630 and voltage impedance electrodes 640 may be connected to the external computing device through wires that may be located either on the inside of the needle or the outside of the needle. If connected on the outside of the needle, the connection may be made by printing tracks of metal conductor over the needle shaft and covering with an insulation material. The impedance-EMG needle may still include an active EMG electrode 610 on the distal end of the shaft 600, and a reference EMG electrode may be located on the skin of the patient.

Figure 7:
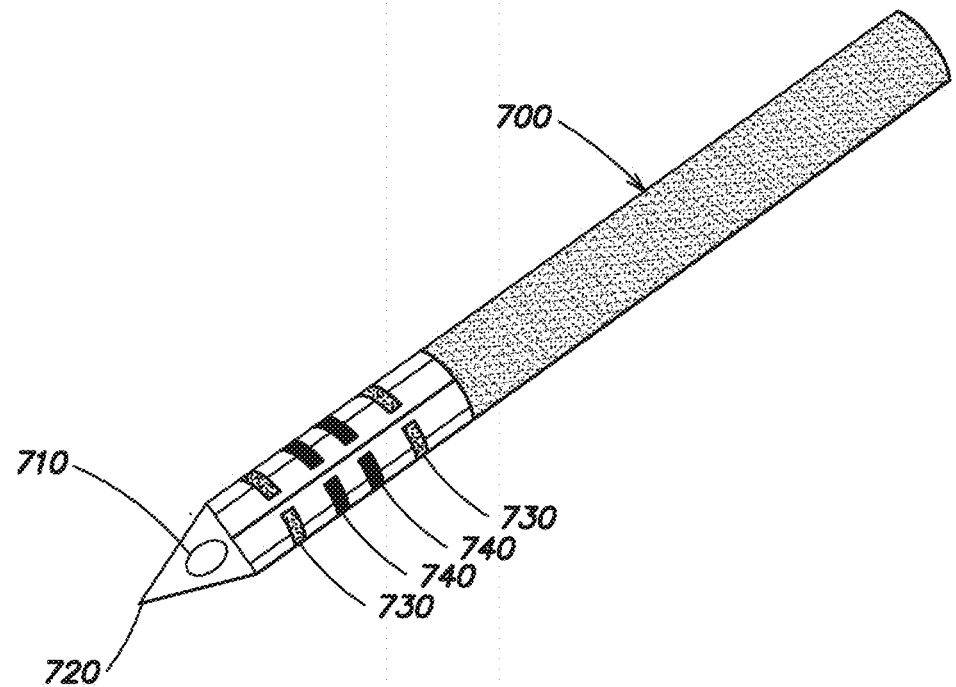
FIG. 7 illustrates an embodiment in which the impedance electrodes are open rings on the impedance-EMG needle.

FIG. 7 illustrates an embodiment in which the current impedance electrodes 730 and voltage impedance electrodes 740 are designed as open rings around the impedance-EMG needle. In such an embodiment, the current impedance electrodes 730 and voltage impedance electrodes 740 may be rings that do not fully encircle the impedance-EMG needle. In this way, the current impedance electrodes 730 and voltage impedance electrodes may be connected to the external computing device through wires that may be located either on the inside of the needle or the outside of the needle. If connected on the outside of the needle, the connection may be made by printing tracks of metal conductor over the needle shaft and covering with an insulation material. The impedance-EMG needle may still include an active EMG electrode 710 on the distal end 720 of the shaft 700, and a reference EMG electrode may be located on the skin of the patient.

Figure 8:
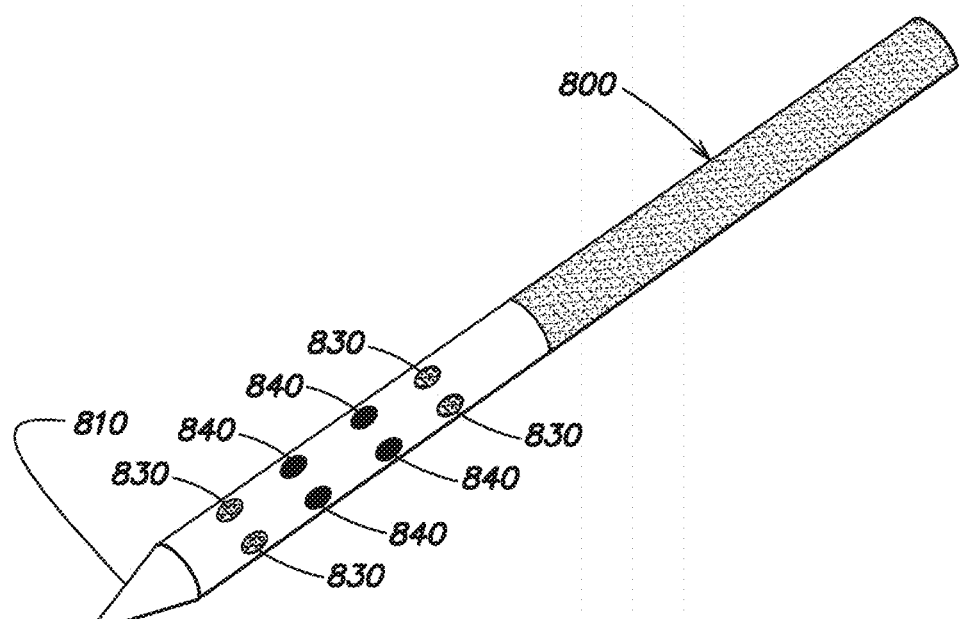
FIG. 8 illustrates an embodiment in which the impedance-EMG needle includes more than four impedance electrodes.

FIG. 8 illustrates an embodiment in which the impedance-EMG needle includes more than four impedance electrodes. In such an embodiment, as shown in FIG. 8, there may exist eight total impedance electrodes. There may be four total current impedance electrodes 830 and four total voltage impedance electrodes 840. This may allow for the impedance-EMG needle to record impedance in different directions and electrode configurations. In doing so, the impedance-EMG needle may be able to obtain measurements that reflect anisotropic properties of the tissue being measured. While this embodiment shows an impedance-EMG needle with eight total impedance electrodes, there may exist more (e.g. sixteen) or fewer (e.g. four) impedance electrodes. The impedance-EMG needle may still include an active EMG electrode 810 on the distal end of the shaft 800, and a reference EMG electrode may be located on the skin of the patient.

Figure 9:
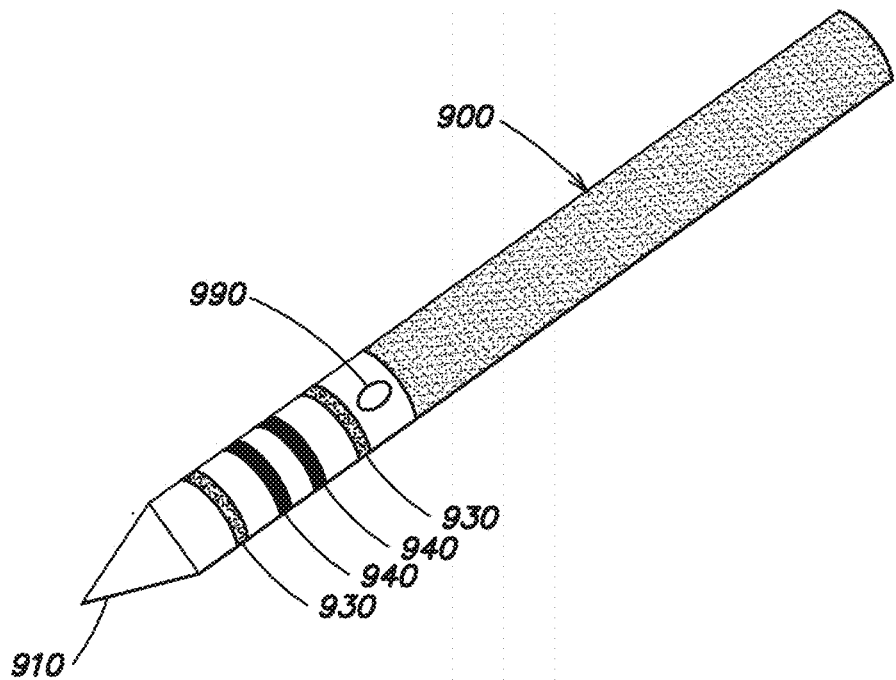
FIG. 9 illustrates an embodiment in which the impedance-EMG needle includes an electrochemical biosensor.\

FIG. 9 illustrates an embodiment in which the impedance-EMG needle includes an electrochemical biosensor 990. The electrochemical biosensor 990 may allow for detection of an analyte that combines a biological component with a physicochemical detector. For example, the electrochemical biosensor 990 may detect cell receptors, enzymes, or nucleid acids in the muscle. The impedance-EMG needle of FIG. 9 includes just one electrochemical biosensor 990, however, it should be appreciated that the impedance-EMG needle may include multiple electrochemical biosensors 990. In such an embodiment, the impedance-EMG needle may still include current impedance electrodes 930 and voltage impedance electrodes 940. In such an embodiment, the impedance-EMG needle may still include current impedance electrodes 930 and voltage impedance electrodes 940. The impedance-EMG needle may also include an active EMG electrode 910 on the distal end of the shaft 900, and a reference EMG electrode may be located on the skin of the patient.

Along with measuring the impedance of muscle tissue, measuring the underlying permittivity of biological tissues and fluids may be essential to understanding how electromagnetic fields interact with biological systems. The permittivity of biological tissue may be determined by the conductivity $\sigma$ (or the resistivity $\rho$ and the relative permittivity $\varepsilon_r$ (or reactivity $\tau$) of the tissue. Various measuring techniques have shown that these properties have a dependence on frequency. An important property of biological tissue is the preference of the electrical current towards flowing in a certain direction. This phenomenon is determined by the anisotropy (i.e. the directional dependence) of the tissue's conductivity and relative permittivity. In skeletal muscle tissue, the anisotropy in these properties may be determined by the orientation of the muscle fibers. For example, an in vivo study in rat muscle reported a ten-fold difference between longitudinal (current flow along the muscle fibers) and transverse (current flow perpendicular to the muscle fibers) conductivity values.

More recently, major efforts have been made to establish a reliable reference database of conductivity and relative permittivity of biological tissue. Among the results reported in these studies, there is a need to develop an improved measurement technique and its specific application to measure the anisotropy in muscle tissue. Indeed, the impedance approaches currently available for measuring in situ the anisotropy of the permittivity of tissues are limited. There are numerous drawbacks to current approaches. First, the approaches available are developed only considering a purely conductive anisotropic material. In reality, living cells interact with the applied electric field and cause a phase-delay that is associated with the tissue's relative permittivity. Second, regarding the investigation of the anisotropic nature of tissue, existing approaches require perfect alignment of electrodes in the longitudinal and transverse directions defined by the unknown tissue's permittivity. According to the type of tissue and a lack of a priori knowledge, it may be difficult or even impossible to perfectly align the electrodes. Third, existing approaches for calculating the conductivity of tissues are based on scaling two apparent conductivity values measured in the longitudinal and transverse directions defined by the unknown tissue's permittivity. Noise, artifacts, and experimental errors in aligning the electrodes may compromise the accuracy of the estimated longitudinal and/or transverse conductivity of the tissue.

Above, embodiments of an impedance-EMG needle in which both EMG electrodes and impedance electrodes are disposed on a single needle have been described. However, in some embodiments, a needle may only have impedance electrodes. For example, in some embodiments, an impedance needle may have two or four impedance electrodes disposed on a needle.

When the anisotropy directions of muscle tissue are assumed to be unknown (the most general case), it may be necessary to measure the impedance of muscle with the impedance needle in three or more directions in order to calculate the permittivity. Otherwise, the error in positioning the impedance probe may compromise the validity of the complex permittivity calculated. However, if the impedance electrodes are disposed on a needle including a monopolar EMG design, as is the case with needles used in needle EMG, this may require at least twelve needle insertions to access inner tissues from the outside. While this may be acceptable in pre-clinical studies, for example to access skeletal muscle tissue through the skin and subcutaneous fat tissues, the clinical translations of these methods may require to reduce the number of insertions to minimize patient discomfort.

The electrical potential $V \in C(V)$ created by a point current electrode in a homogenous and (semi-)infinite anisotropic conductor along the y-axis with relative permittivity $\varepsilon r \in R_{>0}$ (dimensionless) is $$V = \frac{k_\alpha I}{K|r_\alpha|}$$

where $I(A)$ is the total current; $k_\alpha^2 = k_T k_L$ is the geometric mean impedivity from the impedivity in the longitudinal (L) y direction ($\varphi_L$) and transverse (T) $\{x, z\}$ directions ($\varphi_T$); $K \in \{2\pi, 4\pi\}$ is the constant factor for semi-infinite and infinite domains, respectively; and $r_\alpha = (x, \alpha y, z)$ is the apparent position.

Conventionally, measuring the complex permittivity of anisotropic tissues is based on considering the z-component of the impedance probe's apparent position $r_\alpha$ to be zero. In other words, existing methods require to place the impedance probe on the xy-plane. Then, in order to obtain anisotropy information, the apparent impedivity in two or more different directions is measured.

Figure 10A:
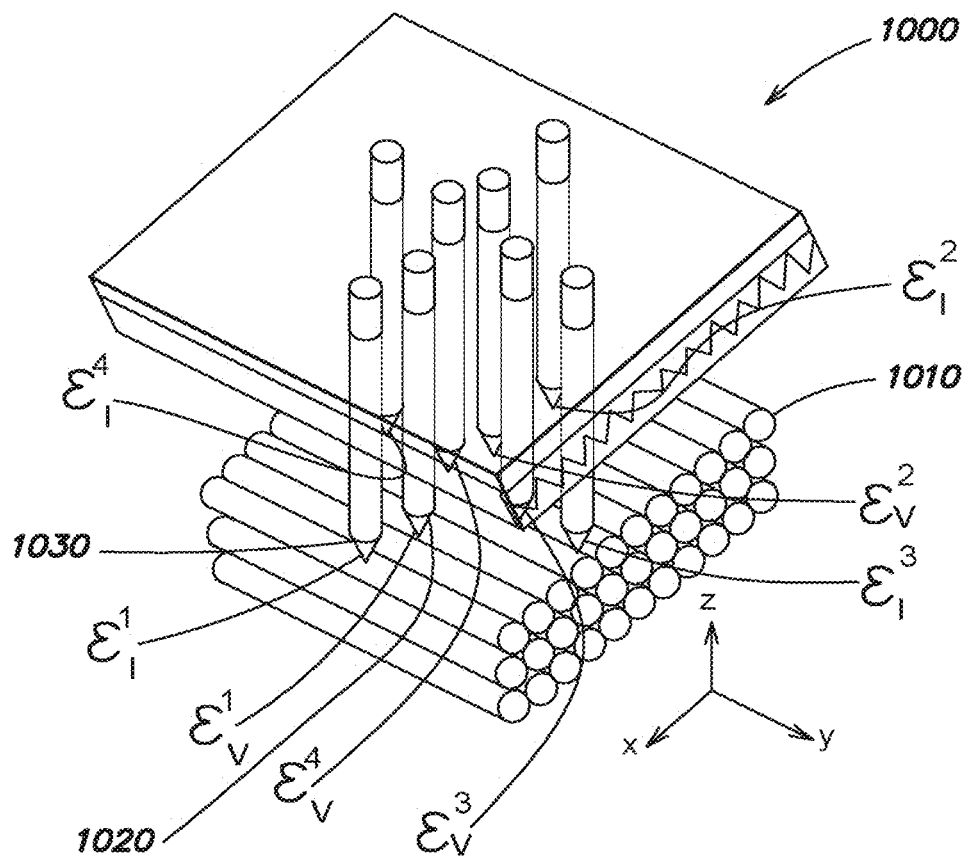
FIG. 10A illustrates a conventional system in which a plurality of impedance needles are inserted into tissue.
Figure 10B:
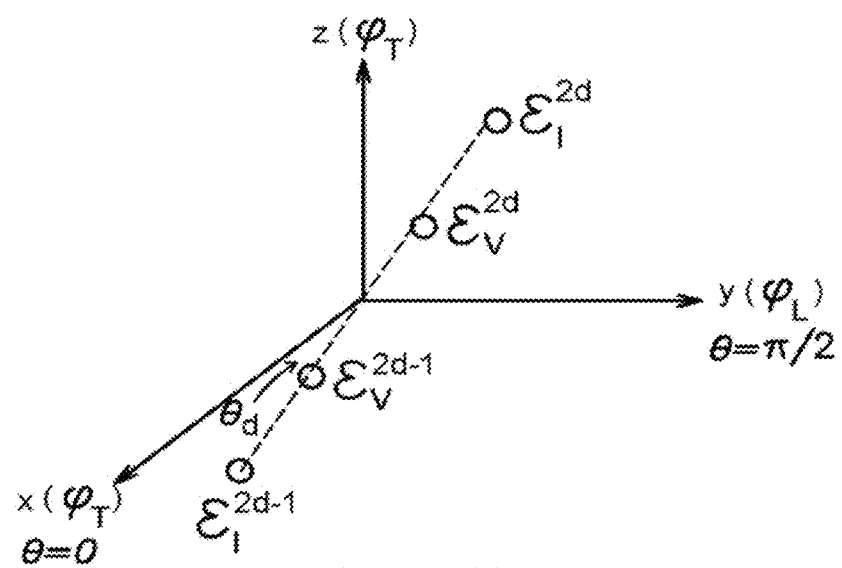
FIG. 10B illustrates a schematic of taking impedance measurements in the system shown in FIG. 10A.

For example, FIG. 10A illustrates a conventional system 1000 in which a plurality of impedance needles are inserted into tissue 1010. The plurality of impedance needles includes a plurality of inner impedance needles 1020 and a plurality of outer impedance needles 1030. The plurality of inner impedance needles 1020 may include at least one voltage impedance electrode, and the plurality of outer impedance needles 1030 may include at least one current impedance electrode. In the system 1010, the plurality of inner impedance needles 1020 and the plurality of outer impedance needles 1030 are inserted into the same depth of the tissue 1010, and the current impedance electrodes and the voltage impedance electrodes are in the xy-plane. FIG. 10B illustrates a schematic of a d-th angle $\theta_d$ of impedance measurement in the xy-plane with respect to the muscle fibers' transverse ($\varphi_T$) and longitudinal ($\varphi_L$) directions.

Figure 11A:
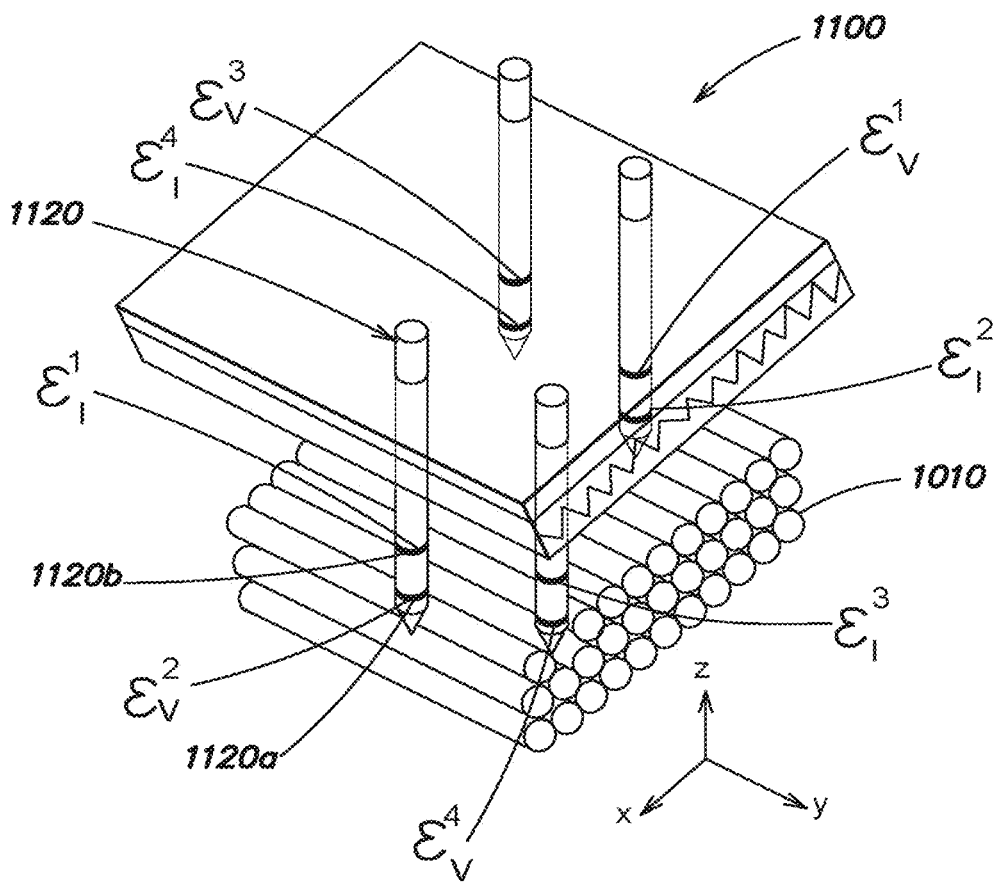
FIG. 11A illustrates a system in which a plurality of impedance needles are inserted into tissue.
Figure 11B:
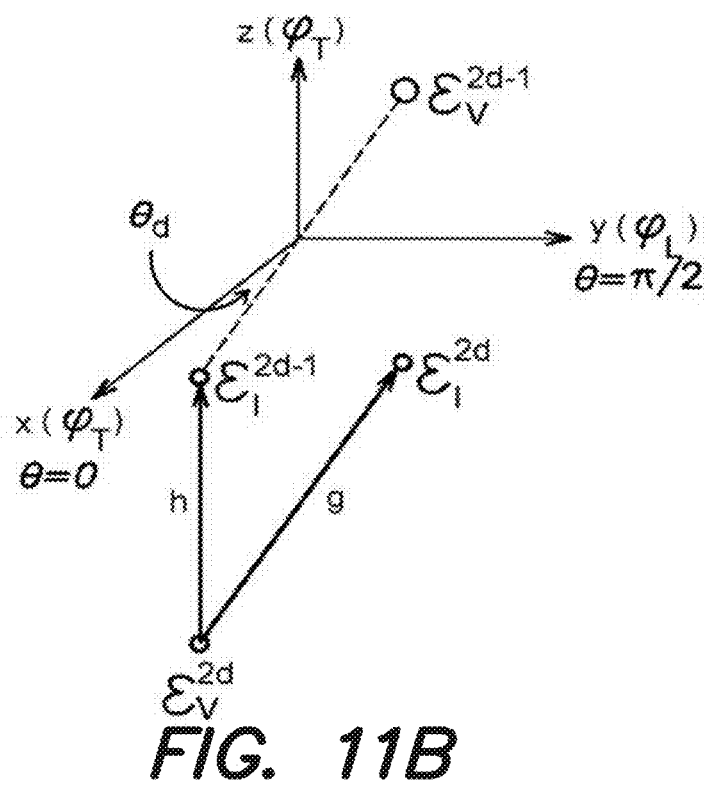
FIG. 11B illustrates a schematic of taking impedance measurements in the system shown in FIG. 11A.

However, in some embodiments, it may be advantageous to insert the impedance probe at varying depths in tissue by changing the z-coordinate. For example, in some embodiments, an impedance needle may have two electrodes—a current impedance electrode and a voltage impedance electrode—spaced along the needle. FIG. 11A illustrates a system 1100 in which a plurality of impedance needles 1120 are inserted into tissue 1110. In some embodiments, the plurality of impedance needles may include at least one voltage impedance electrode 1120a and at least one current impedance electrode 1120b. In some embodiments, the plurality of impedance needles 1120 may be inserted into the tissue 1110 such that the at least one voltage impedance electrode 1120a and the at least one current impedance electrode 1120b are at different depths in the tissue 1110 (e.g., they have different z-coordinates). FIG. 11B illustrates a schematic of a d-th angle $\theta_d$ of impedance measurement in the xy-plane with respect to the muscle fibers' transverse ($\varphi_T$) and longitudinal ($\varphi_L$) directions.

In some embodiments of the system 1100, the impedance may be measured at two angles $\theta$ equal to the muscle fibers' transverse ($\varphi_T$) and longitudinal ($\varphi_L$) directions. In other embodiments, the impedance may be measured at any pair of angles $\theta$. In another embodiment, the impedance may be measured at more than two angles $\theta$.

Figure 12A:
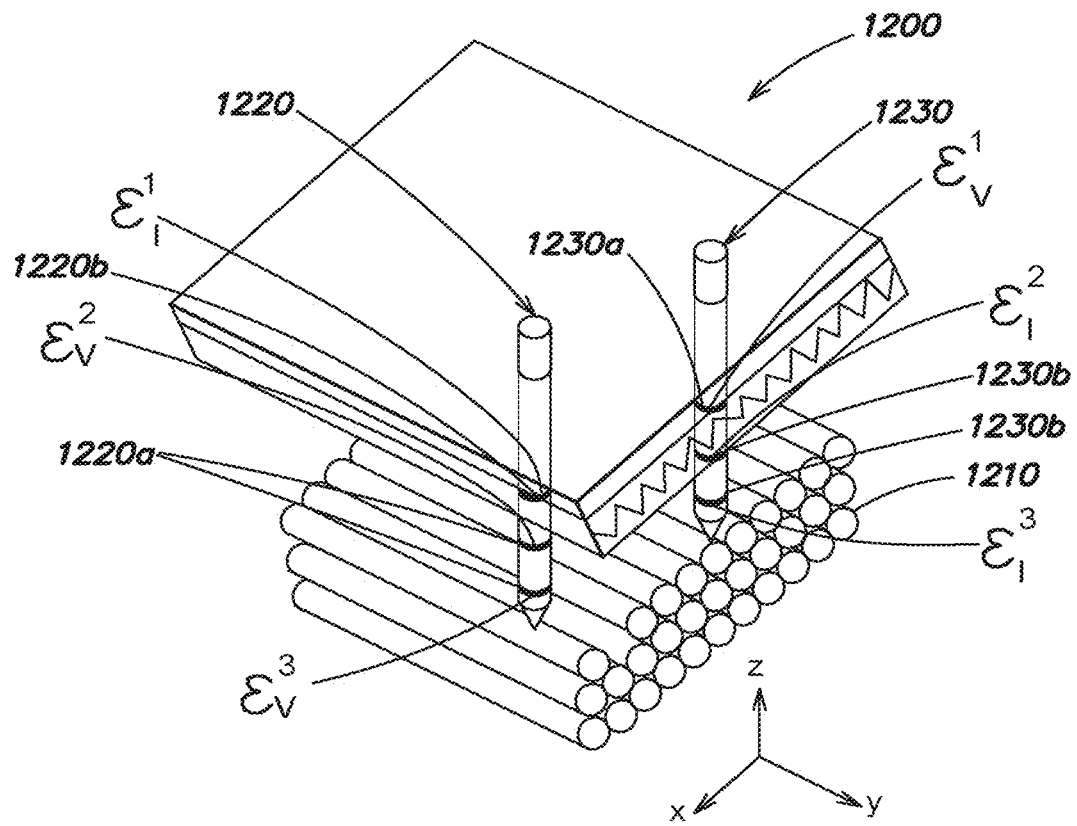
FIG. 12A illustrates a system in which a plurality of impedance needles are inserted into tissue.
Figure 12B:
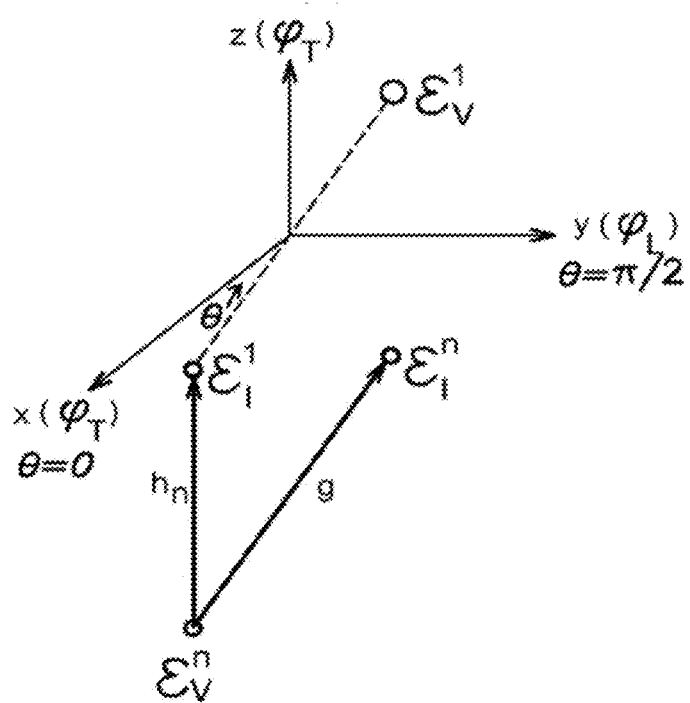
FIG. 12B illustrates a schematic of taking impedance measurements in the system shown in FIG. 12A.

In some embodiments, it may be advantageous for the impedance needle to have multiple voltage impedance electrodes and/or multiple current impedance electrodes. For example, if the distance between two electrodes on an impedance needle is d, and the impedance needle has a plurality of electrodes, then the distance between the outer electrodes on the impedance needle is equal to Nd, wherein N can be considered the number of inter-electrode distances. FIG. 12A illustrates a system 1200 in which a first impedance needle 1220 and a second impedance needle 1230 are inserted into tissue 1210. In some embodiments, the first impedance needle 1220 may include two voltage impedance electrodes 1220a and one current impedance electrode 1220b. In some embodiments, the second impedance needle 1230 may include one voltage impedance electrode 1230a and two current impedance electrodes 1230b. FIG. 12B illustrates a schematic of an n-th inter-electrode distance measured in the z-direction. In FIG. 12B, the measurement angle θ is defined with respect to the transverse {x, z} directions and the longitudinal y direction of the tissue 1210.

In the system 1100 the number of electrodes, and thus the number of inter-electrode distances was constant (N=1), and the impedance measurement angle θ was varied. In the system 1200, however, the impedance measurement angle θ is constant, and the number of inter-electrode distances N within the same impedance needle is varied.

In some embodiments in the system 1200, the impedance may be measured with N=2 inter-electrode distances. In other embodiments, the impedance may be measured with N≥2 inter-electrode distances.

While the first impedance needle 1220 is shown to have two voltage impedance electrodes and one current impedance electrode, it should be appreciated that the first impedance needle 1220 may have a different number of voltage impedance electrodes and current impedance electrodes, as other configurations are possible.

Similarly, while the second impedance needle 1230 is shown to have one voltage impedance electrode and two current impedance electrodes, it should be appreciated that the second impedance needle 1230 may have a different number of voltage impedance electrodes and current impedance electrodes, as other configurations are possible.

In some embodiments, it may be advantageous for the impedance needle to have multiple voltage impedance electrodes and/or multiple current impedance electrodes and to measure impedance at varying inter-electrode distances N, as in the system 1200, as well as to measure the impedance at varying measurement angles θ, as in the system 1100. A feature that previous methods have in common is that it is assumed that one knows the anisotropic direction of the tissue. In other words, when the measuring angles θ are π/2 and 0, the apparent impedivity measured is that corresponding to the longitudinal and transverse directions defined by the tissue's resistivity and reactivity properties. Subsequently, experimental errors positioning the needle electrodes with respect to the anisotropy in the permittivity of the tissue may give inaccurate estimates. This limitation may be overcome by measuring the apparent impedivity of the tissue with multiple inter-electrode distances N and multiple measurement angles θ.

Figure 13A:
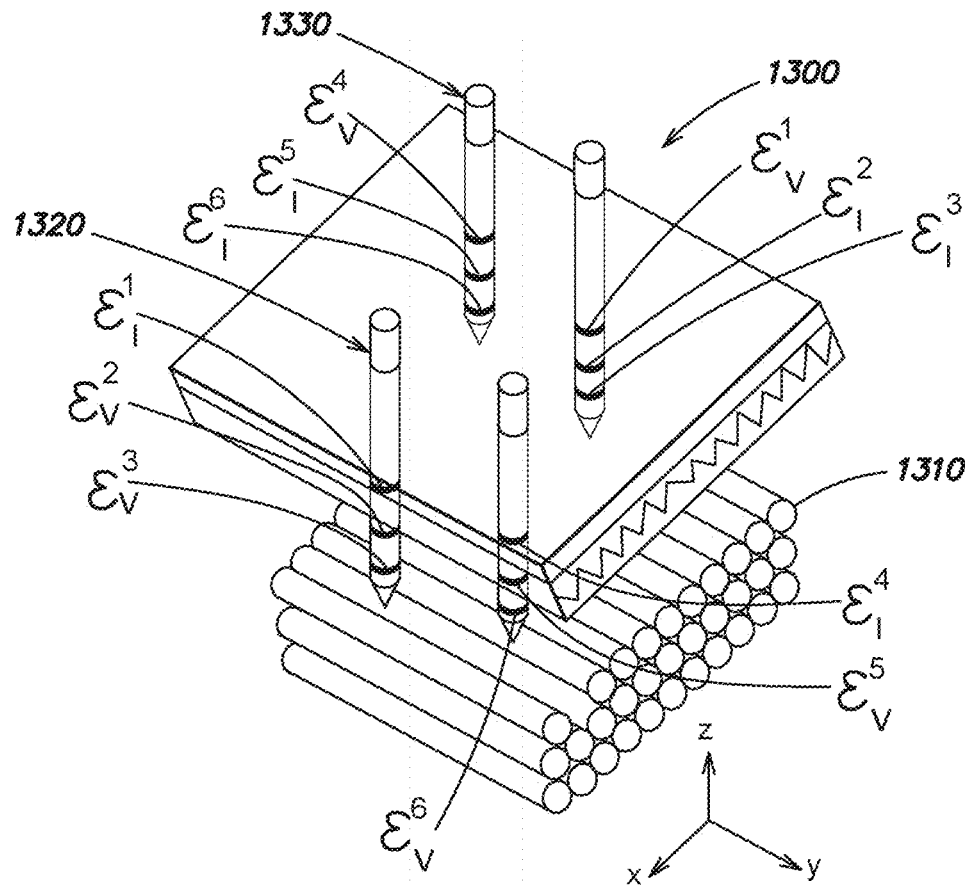
FIG. 13A illustrates a system in which a plurality of impedance needles are inserted into tissue.
Figure 13B:
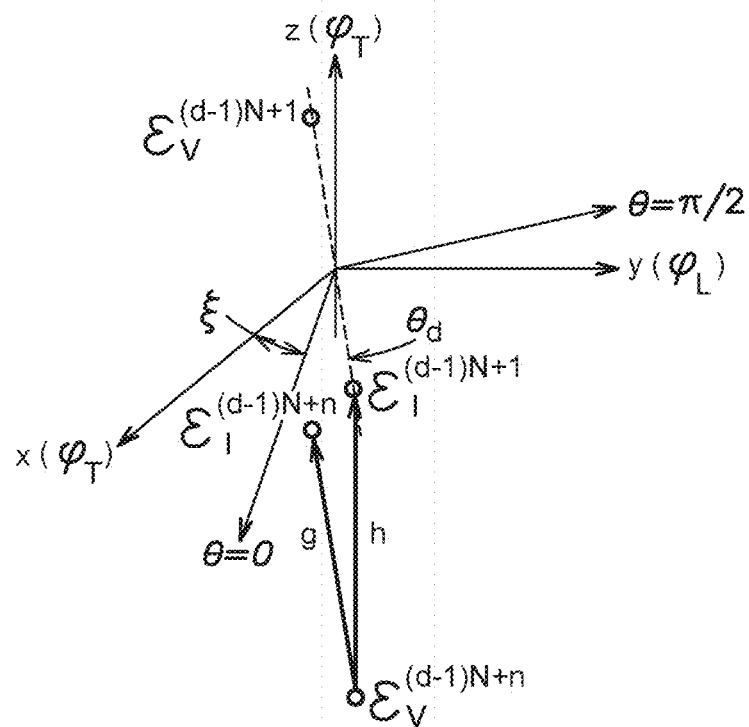
FIG. 13B illustrates a schematic of taking impedance measurements in the system shown in FIG. 13A.

For example, FIG. 13A illustrates a system 1300 in which a plurality of impedance needles are inserted into tissue 1310. In some embodiments, the plurality of impedance needles may include at least two first impedance needles 1320 and at least two second impedance needles 1330. Similar to the first impedance needle 1220 and the second impedance needle 1230 of FIG. 12A, the at least two first impedance needles 1320 may include two voltage impedance electrodes and one current impedance electrode, and the at least two second impedance needles 1330 may include one voltage impedance electrode and two current impedance electrodes. FIG. 13B illustrates a schematic of an n-th inter-electrode distance and d-th angle measured. In FIG. 13B, the measurement angle $θ_d$ is defined with respect to the unknown transverse and longitudinal directions of the tissue 1310. In some embodiments in the system 1300, the impedance may be measured with N≥2 inter-electrode distances and D≥3 measurement angles.

In some embodiments, the impedance needle may be a probe having four impedance electrodes, or a "four-electrode probe." For example, the impedance needle may have a configuration of impedance electrodes similar to the impedance-EMG needle as described herein. In some embodiments, the plurality of impedance needles may be inserted into the tissue 1310 at a depth of approximately 45 mm, and impedance data may be taken across multiple frequencies. In some embodiments, the distance between the four electrodes of the impedance needle may, ordering the electrodes from the tip of the needle to the base of the needle, be 1.5 mm, 2 mm, and 1.5 mm.

In some embodiments, various configurations of the electrodes in the four-electrode probe may be utilized for measuring in situ the anisotropic permittivity. In the table below, some example configurations are shown. In various configurations, different electrodes may be either HC (high (source) current), HP (high (positive) potential), LP (low (negative) potential), LC (low (sink) current), or NC (not connected).

|  |  | $p_1 = g/h_1 = 20$ Electrode | | | | $p_2 = g/h_2 = 8.6$ Electrode | | | | $p_3 = g/h_3 = 6$ Electrode | | | |
| --- | --- | --- | --- | --- | --- | --- | --- | --- | --- | --- | --- | --- | --- |
|  | Needle | 1 | 2 | 3 | 4 | 1 | 2 | 3 | 4 | 1 | 2 | 3 | 4 |
| $θ_{1,2,3} = 0$, π/4, π/2 | 1 | HC | LP | NC | NC | HC | NC | LP | NC | HC | NC | NC | LP |
|  | 2 | HP | LC | NC | NC | HP | NC | LC | NC | HC | NC | NC | LC |

Measuring muscle tissue's anisotropic permittivity may assist in tracking disease progression and evaluating treatment effect of patients with NMD. In NMD, the pathophysiology of the disease may later the structure and content of muscle tissue, which may change the permittivity of the muscle. For example, Duchenne muscular dystrophy is characterized by the loss of muscle fibers and their progressive substitution by fat and fibrous tissue. Improving the ability to accurately measure muscle permittivity may yield insight into developing strategies for newer diagnostic tools and treatments. Additionally, the described embodiments may assist in reducing the number of needle insertions required to measure muscle permittivity.

Figure 14:
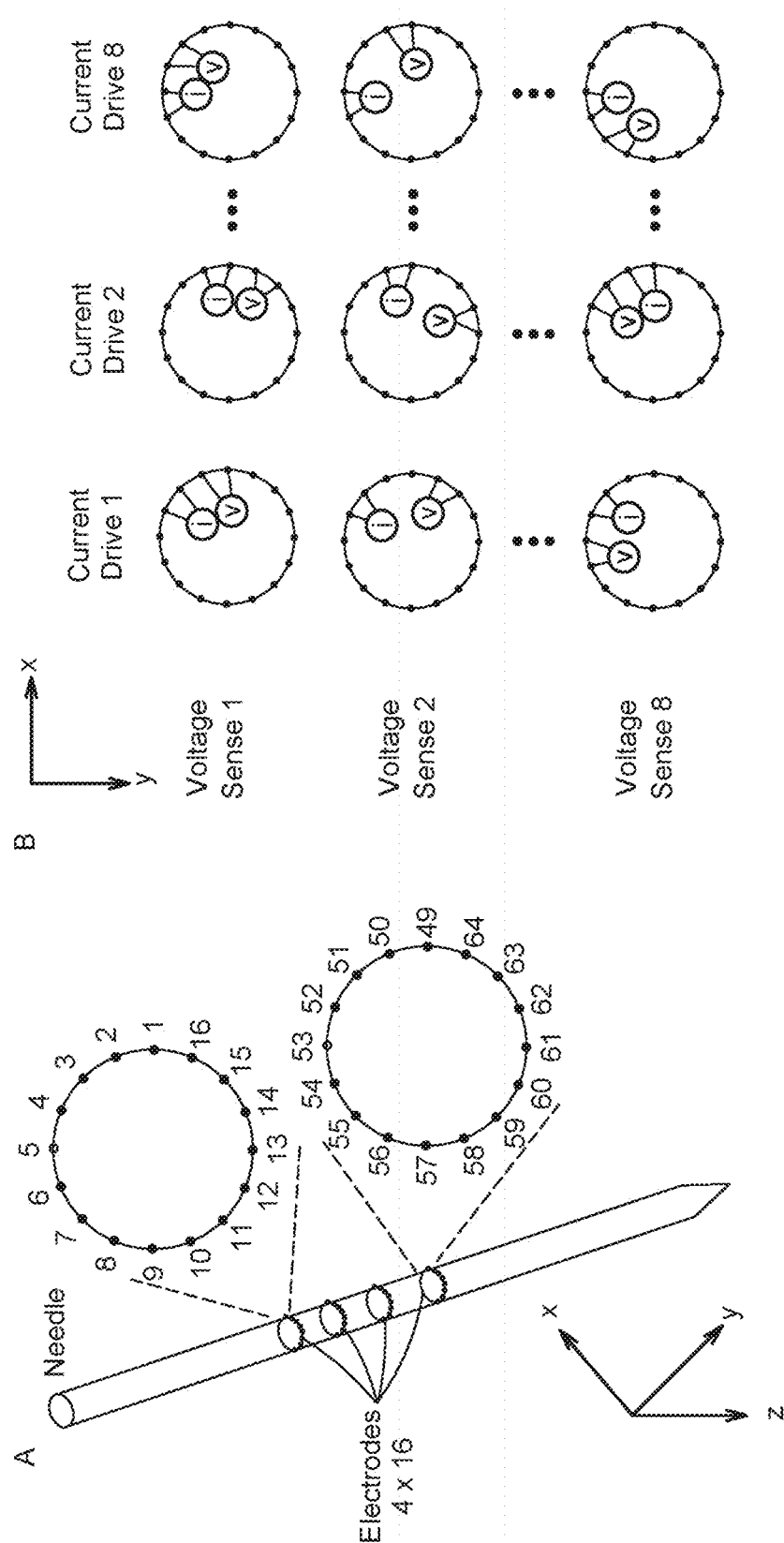
FIG. 14 illustrates an embodiment of an impedance needle having 64 impedance electrodes distributed circumferentially along the needle shaft in 4 planes.

In some embodiments, an impedance needle may be configured to be used for electrical impedance imaging (EII). In such an embodiment, the impedance needle may have a plurality of electrodes, for example arranged in a configuration such that there are electrodes on four different planes perpendicular to the length of the needle. For example, FIG. 14 illustrates an embodiment of an impedance needle having 64 electrodes distributed circumferentially along the needle shaft in 4 planes. In some embodiments, the impedance needle may have additional electrodes configured for EMG measurements. In such an embodiment, the impedance needle may additionally measure EMG in order to generate an image of the tissue.

Developments in imaging techniques over the past two decades have enhanced the diagnosis and evaluation of muscle disorders. Two of the most commonly used imaging modalities, magnetic resonance imaging (MRI) and ultrasound (US), have received increasing attention in both clinical neuromuscular care and research. MRI has shown versatility due to its ability to assist in disease diagnosis, as a biomarker of disease progression, and as a tool to assess metabolic alterations. Similarly, US and its variations, including elastography and quantitative US, are of interest given its ease of use and capability to track primary muscle disease progression and response to therapy. There are, however, technical and practical limitations associated with the use of MRI and US. For example, MRI is relatively time-intensive to complete, costly, requires patients to go to a specialized facility, and requires patients to be still for several minutes at a time. In contrast, US can be performed conveniently at the bedside—however, slight alterations in the probe angle can distort the image and requires considerable examiner experience to performed adequately.

One modality well-suited for evaluating muscle is EII. In EII, a weak, non-ionizing electrical current (typically between 10 and 100 kHz) may be applied across two drive electrodes, and the resulting voltage may be measured by two or more pairs of sense electrodes. This procedure may be then repeated multiple times, sequentially changing the driving and sensing electrodes until an entire circle has been completed. For example, FIG. 14 shows a plurality of modes in which different pairs of the impedance electrodes on the impedance needle are configured to drive a current and to sense voltage. From this data obtained across multiple electrodes, an image can be reconstructed using a mathematical algorithm.

Like MRI and US, the standard approach to employing EII consists of creating impedance images of internal structures from non-invasive surface recordings—i.e., an "outside-in" approach. While clearly valuable, this approach may be cumbersome to apply in practice since it requires placement of 8, 16, 32, or up to 64 electrodes over a body region. In some embodiments, an "inside-out" approach may be employed, in which the current-driving and voltage-sensing electrodes may be embedded within the impedance needle that is inserted into the muscle. The impedance image created may represent a volume surrounding the impedance needle and could potentially detect intrusions of fat deposition, connective tissue, or regions of inflammation. Thus, like in needle EMG, "needle EII" may be used at the bedside of a patient to interrogate the muscle, from which impedance images of muscle may be reconstructed in real time, revealing alterations at the micrometer scale that may only be typically observable via direct biopsy.

Figure 15:
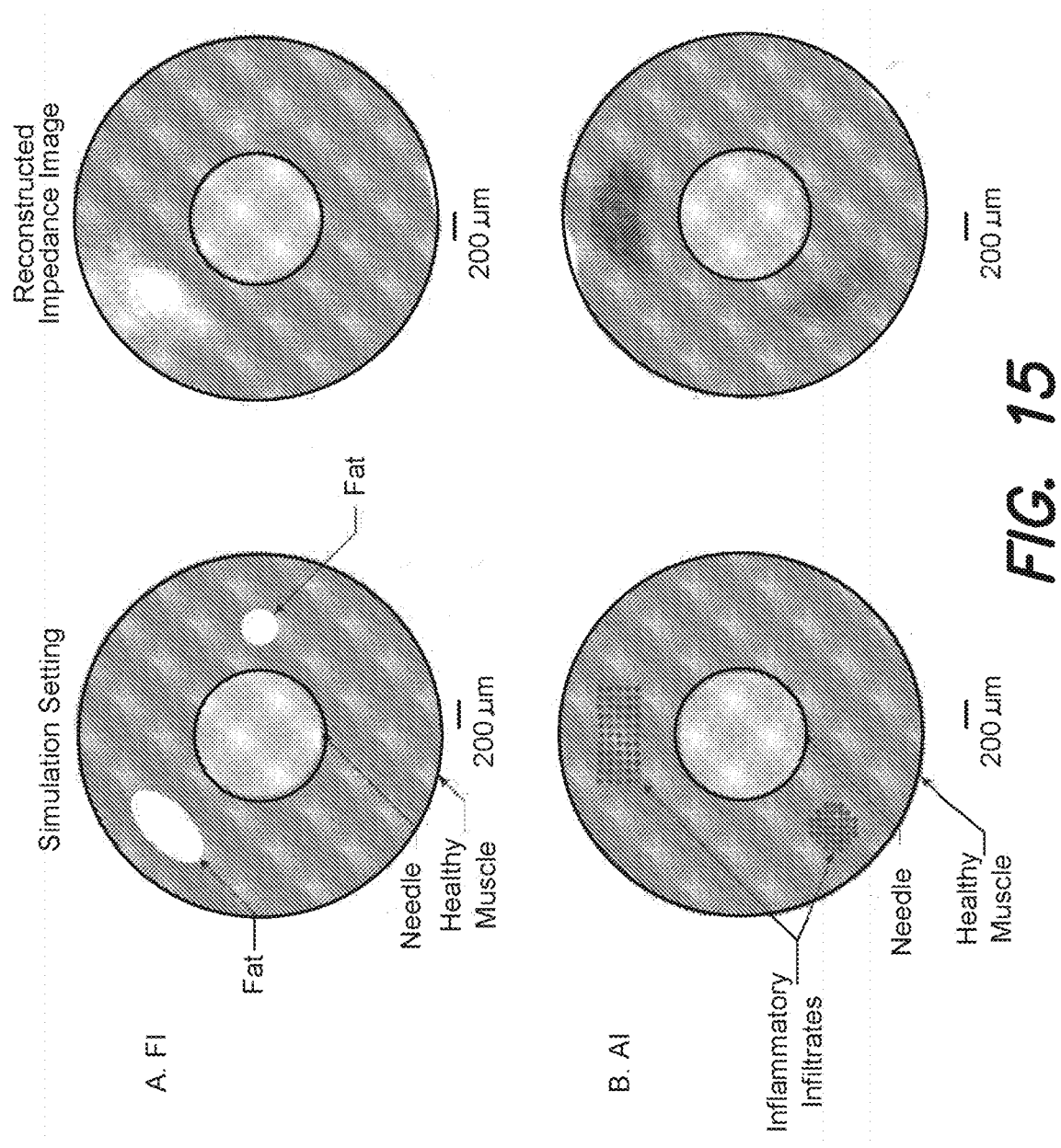
FIG. 15 illustrates an example of a comparison of images generated through needle EIi with images generated through finite element model (FEM) simulation incorporating human anatomical constraints.

FIG. 15 illustrates an example of a comparison of images generated through needle EII with images generated through finite element model (FEM) simulation incorporating human anatomical constraints. FEMs of the human right arm with a 19G needle inserted into the center of the long head of triceps brachii muscle were generated. The FEM model was created from MR images of the right arm of a healthy subject. Two simplified states of muscle were evaluated: one with a region of fatty infiltration (A. FI), and one with a region of acute inflammation/edema (B. AI). In the FI case, fat deposition was simulated with less conductive regions as compared to areas of healthy muscle tissue. In the AI case, edema was simulated with intrusions of more conductive regions in the muscle, whereas the surrounding tissue was simulated as healthy muscle tissue. In both FEMs, the inherent electrical properties of muscle and its anisotropy were taken from an online reference database. To generate the impedance images shown in FIG. 15, the impedance needle may have 16 impedance electrodes distributed circumferentially along the needle shaft in 4 different planes, giving a total of 64 electrodes, as shown in FIG. 14. A rotational scheme may be implemented to generate the impedance images. To generate the impedance images, electrical current may be applied across two drive electrodes of the impedance needle and the resulting voltage may be measured using a second pair of sense electrodes of the impedance needle. The procedure may be repeated applying current between pairs of adjacent electrodes until an entire circle has been completed. Then, image reconstruction may be carried out using a mathematical algorithm to visualize the internal impedance distribution of muscle. Additionally, the impedance needle may include at least one EMG electrode configured to measure EMG of the muscle, and the image may be reconstructed from the EMG measurements as well.

Figure 16:
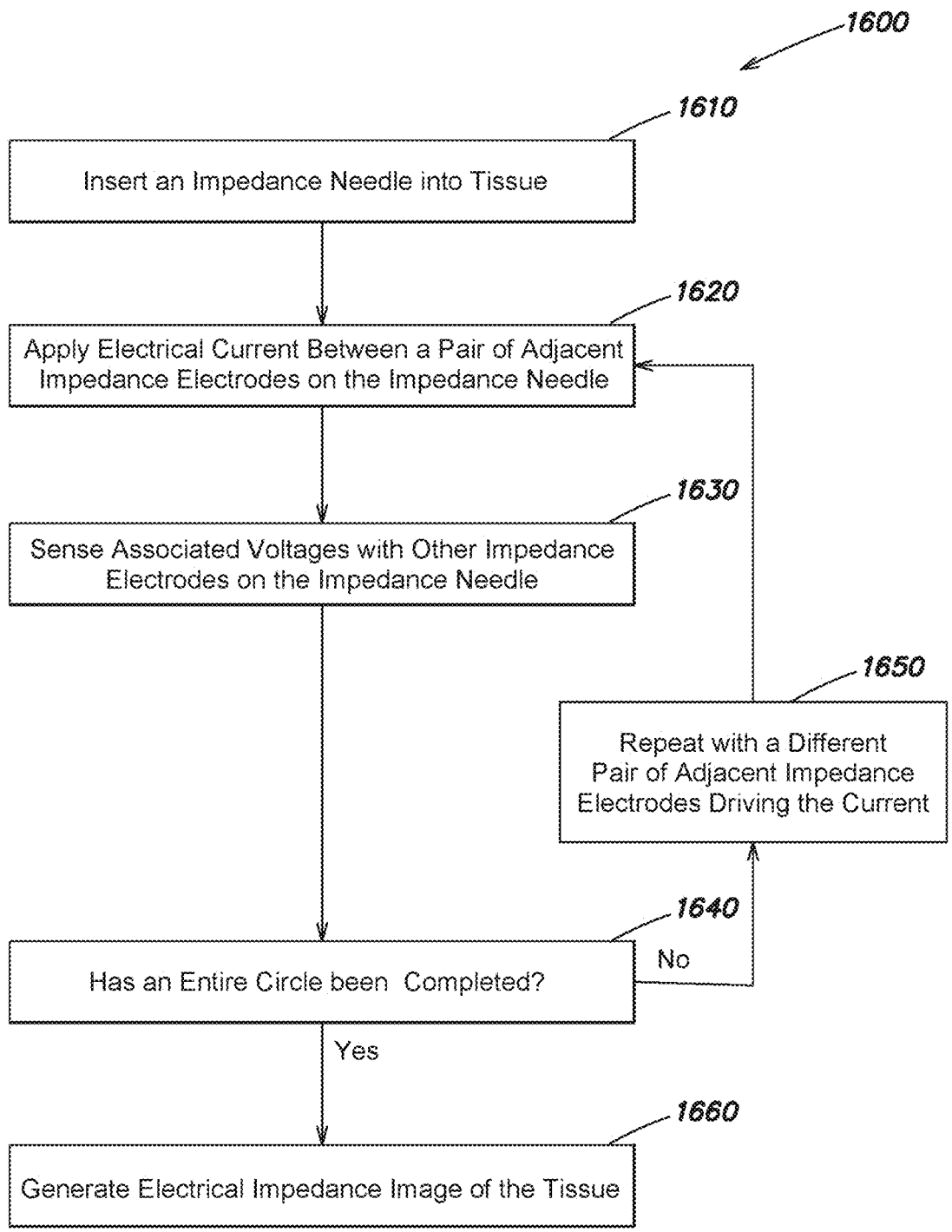
FIG. 16 is a flow chart of an example process for generating an electrical impedance image using an impedance needle.

For example, FIG. 16 is a flow chart of an example process 1600 for generating an electrical impedance image using an impedance needle. In some embodiments, the process 1600 may include a step 1610, in which an impedance needle is inserted into tissue. The process 1600 may then include a step 1620, in which an electrical current is applied between a pair of adjacent impedance electrodes in the impedance needle. The process 1600 may then include a step 1630, in which associated voltages are sensed by other impedance electrodes on the impedance needle. The process 1600 may then include a step 1640, in which it is determined whether an entire circle of impedance measurements has been completed. If not, the process 1600 may proceed to a step 1650, in which the process 1600 returns to step 1620, but with a different pair of adjacent impedance electrodes driving the current. If a circle of impedance measurements has been completed, the process 1600 may proceed to a step 1660, in which an electrical impedance image of the tissue is generated.

In some embodiments, an image reconstruction method may include a two-step algorithm to construct a linear system $S_\kappa = Z$, where K represents the muscle impedance to be reconstructed, S is the impedance sensitivity matrix obtained from vertical impedance measurements, and Z is the impedance data obtained with the rotation scheme shown in FIG. 14. In the first step, the domain may be discretized and S may be calculated. In the second step, Z may be obtained. Image reconstruction may then be formulated as a linear least-squares model-fitting problem, where the FEM model represents the imaging region and predicts the measured impedances. Specifically, the two-dimensional image reconstruction may be formulated minimizing the following equation:

$$\min \lVert \overline{S}\overline{\kappa} - \overline{Z} \rVert^2 + \lambda \lVert \overline{W}\overline{\kappa} - \overline{k} \rVert^2$$

where $\overline{\kappa}$ is the reconstructed impedance of anisotropic muscle, $\overline{S}$ is the impedance sensitivity matrix obtained from the equation above, $\lambda$ is the regularization parameter, $\overline{W}$ is a regularization matrix, $\overline{k}$ is the prior knowledge on $\overline{\kappa}$, and $\lVert \cdot \rVert$ is L2 norm. This approach may be defined as a static two-dimensional imaging in which $\overline{\kappa}$ at position (x, y) is estimated.

FIG. 15 shows reconstructed impedance images, and their comparison to the FEM simulations. In both the simulation setting with fatty infiltration (A. FI) and acute inflammation/edema (B. AI), it is possible to distinguish the anomaly in the muscle with needle EII, showing areas of reduced conductivity in the fat-infiltrated muscle and areas of increased conductivity in the muscle impacted by acute inflammation/edema.

Using the impedance needle described herein, the potential of EII to image confined regions of muscle has been demonstrated. The results at 50 kHz show it is possible to detect and image microscopic muscle alterations, including the presence of regions of inflammation and fat deposition.

While 50 kHz may be used for impedance imaging, other frequencies may be used (e.g., 100 kHz), as the impedivity properties of tissues may not change sufficiently with frequencies approximate to the range used. Furthermore, in using an impedance needle, both superficial and deep muscles may be imaged, as the impedance data may be minimally disturbed by other tissues such as skin and subcutaneous fat. These disturbances may be more significant in attempting to use EII with impedance electrodes on a patient's skin. Needle EII may provide novel insights into muscle condition by imaging muscle structure and composition at the bedside that may otherwise likely only be obtainable with biopsy. Needle EII may also be capable of generating an impedance image with higher resolution than other impedance images generated using other techniques.

In some embodiments, an impedance needle (e.g., the impedance needle described in connection with FIG. 14) may be configured to measure the anisotropic permittivity of muscle. For example, a method may include a first step of estimating the impedivity of anisotropic muscle to obtain the actual impedivity distribution. In some embodiments, estimating the impedivity may comprise estimating the longitudinal (L) impedivity $$\hat{\kappa}_L := \hat{\alpha}\hat{\kappa}_\alpha$$

and estimating the transverse (T) impedivity $$\hat{\kappa}_T := \frac{\hat{\kappa}_\alpha}{\hat{\alpha}}$$

of anisotropic muscle from vertical impedance measurements, where $\hat{\kappa}_\alpha$ and $\hat{\alpha}^2$ are the estimated geometric mean impedivity and the estimated anisotropy ratio of muscle, respectively, defined as $$\begin{cases} \hat{\kappa}_\alpha := \frac{1}{D}\sum_{n=1}^{D} Z_n K d \\ \hat{\alpha}^2 := \frac{1}{D}\sum_{n=1}^{D} \frac{1}{\cos^2 A_n}\left[\frac{(2\hat{\kappa}_\alpha d_e)^2}{4r^2\sin^2 B(Z_n K d + 2\hat{\kappa}_\alpha)^2} - \sin^2 A_n\right] \end{cases}$$

with $Z_n$ the measured impedance using the nth electrode configuration, $K=4\pi$ is a scaling factor, $d_e$ is electrode depth distance, D is the number of electrodes within the same plane, r is the needle radius, $A_n:=(\theta_n+\theta_{n+1})/2$ and $B:=(\theta_n-\theta_{n+1})/2$.

In some embodiments, the method includes a second step of measuring the impedance data with the impedance needle, using a rotational scheme as described in connection with FIG. 14. Image reconstruction may then be formulated as a linear least-squares model fitting problem.

As discussed, needle EII may be used as a bedside diagnostic tool to help evaluate the condition of a region of muscle. The EII needle may be guided using US and moved around within the muscle while imaging, so as to have a broader field of view. EII could also be used as a biomarker for evaluating the impact of novel therapies in the treatment of muscle condition, including muscular dystrophies. EII may also be integrated into EMG needle devices to image the microstructure of muscle and alterations with disease at the same time EMG is recorded.

In some embodiments, the impedance-EMG needle and/or the impedance needle, as described above, may be configured to measure the temperature of tissue. For example, the impedance-EMG needle and/or the impedance needle may include an additional electrode to measure the temperature, or the temperature may be measured from two electrodes on the impedance-EMG needle and/or the impedance needle.

Additionally, the impedance electrodes described in connection with the impedance-EMG needle and/or the impedance needle may be configured to perform EMG measurements as well, if necessary.

Embodiments of the impedance-EMG needle and/or the impedance needle may be additionally configured to assess non-muscular structures in tissue. For example, the impedance-EMG needle and/or the impedance needle may be configured to assess fat, or foreign objects such as blood clots and/or other masses. The impedance-EMG needle and/or the impedance needle may also be configured to determine if the impedance-EMG needle and/or the impedance needle has been inadvertently been stuck into a tendon, or a blood vessel, or other unintended tissue. The impedance-EMG needle and/or the impedance needle may be configured to assist with accurate needle localization.

Techniques operating according to the principles described herein may be implemented in any suitable manner. Included in the discussion above are a series of flow charts showing the steps and acts of various processes that use both EMG and impedance to measure electrical properties of tissue and evaluate neuromuscular disease, as well as processes for needle EII. The processing and decision blocks of the flow charts above represent steps and acts that may be included in algorithms that carry out these various processes. Algorithms derived from these processes may be implemented as software integrated with and directing the operation of one or more single- or multi-purpose processors, may be implemented as functionally-equivalent circuits such as a Digital Signal Processing (DSP) circuit or an Application-Specific Integrated Circuit (ASIC), or may be implemented in any other suitable manner. It should be appreciated that the flow charts included herein do not depict the syntax or operation of any particular circuit or of any particular programming language or type of programming language. Rather, the flow charts illustrate the functional information one skilled in the art may use to fabricate circuits or to implement computer software algorithms to perform the processing of a particular apparatus carrying out the types of techniques described herein. It should also be appreciated that, unless otherwise indicated herein, the particular sequence of steps and/or acts described in each flow chart is merely illustrative of the algorithms that may be implemented and can be varied in implementations and embodiments of the principles described herein.

Accordingly, in some embodiments, the techniques described herein may be embodied in computer-executable instructions implemented as software, including as application software, system software, firmware, middleware, embedded code, or any other suitable type of computer code. Such computer-executable instructions may be written using any of a number of suitable programming languages and/or programming or scripting tools, and also may be compiled as executable machine language code or intermediate code that is executed on a framework or virtual machine.

When techniques described herein are embodied as computer-executable instructions, these computer-executable instructions may be implemented in any suitable manner, including as a number of functional facilities, each providing one or more operations to complete execution of algorithms operating according to these techniques. A "functional facility," however instantiated, is a structural component of a computer system that, when integrated with and executed by one or more computers, causes the one or more computers to perform a specific operational role. A functional facility may be a portion of or an entire software element. For example, a functional facility may be implemented as a function of a process, or as a discrete process, or as any other suitable unit of processing. If techniques described herein are implemented as multiple functional facilities, each functional facility may be implemented in its own way; all need not be implemented the same way. Additionally, these functional facilities may be executed in parallel and/or serially, as appropriate, and may pass information between one another using a shared memory on the computer(s) on which they are executing, using a message passing protocol, or in any other suitable way.

Generally, functional facilities include routines, programs, objects, components, data structures, etc. that perform particular tasks or implement particular abstract data types. Typically, the functionality of the functional facilities may be combined or distributed as desired in the systems in which they operate. In some implementations, one or more functional facilities carrying out techniques herein may together form a complete software package. These functional facilities may, in alternative embodiments, be adapted to interact with other, unrelated functional facilities and/or processes, to implement a software program application. In other implementations, the functional facilities may be adapted to interact with other functional facilities in such a way as form an operating system, including the Windows® operating system, available from the Microsoft® Corporation of Redmond, Wash. In other words, in some implementations, the functional facilities may be implemented alternatively as a portion of or outside of an operating system.

Some exemplary functional facilities have been described herein for carrying out one or more tasks. It should be appreciated, though, that the functional facilities and division of tasks described is merely illustrative of the type of functional facilities that may implement the exemplary techniques described herein, and that embodiments are not limited to being implemented in any specific number, division, or type of functional facilities. In some implementations, all functionality may be implemented in a single functional facility. It should also be appreciated that, in some implementations, some of the functional facilities described herein may be implemented together with or separately from others (i.e., as a single unit or separate units), or some of these functional facilities may not be implemented.

Computer-executable instructions implementing the techniques described herein (when implemented as one or more functional facilities or in any other manner) may, in some embodiments, be encoded on one or more computer-readable media to provide functionality to the media. Computer-readable media include magnetic media such as a hard disk drive, optical media such as a Compact Disk (CD) or a Digital Versatile Disk (DVD), a persistent or non-persistent solid-state memory (e.g., Flash memory, Magnetic RAM, etc.), or any other suitable storage media. Such a computer-readable medium may be implemented in any suitable manner, including as computer-readable storage media 406 of FIG. 4 described above (i.e., as a portion of a computing device 400) or as a stand-alone, separate storage medium. As used herein, "computer-readable media" (also called "computer-readable storage media") refers to tangible storage media. Tangible storage media are non-transitory and have at least one physical, structural component. In a "computer-readable medium," as used herein, at least one physical, structural component has at least one physical property that may be altered in some way during a process of creating the medium with embedded information, a process of recording information thereon, or any other process of encoding the medium with information. For example, a magnetization state of a portion of a physical structure of a computer-readable medium may be altered during a recording process.

Further, some techniques described above comprise acts of storing information (e.g., data and/or instructions) in certain ways for use by these techniques. In some implementations of these techniques—such as implementations where the techniques are implemented as computer-executable instructions—the information may be encoded on a computer-readable storage media. Where specific structures are described herein as advantageous formats in which to store this information, these structures may be used to impart a physical organization of the information when encoded on the storage medium. These advantageous structures may then provide functionality to the storage medium by affecting operations of one or more processors interacting with the information; for example, by increasing the efficiency of computer operations performed by the processor(s).

In some, but not all, implementations in which the techniques may be embodied as computer-executable instructions, these instructions may be executed on one or more suitable computing device(s) operating in any suitable computer system, including the exemplary computer system of FIG. 4, or one or more computing devices (or one or more processors of one or more computing devices) may be programmed to execute the computer-executable instructions. A computing device or processor may be programmed to execute instructions when the instructions are stored in a manner accessible to the computing device or processor, such as in a data store (e.g., an on-chip cache or instruction register, a computer-readable storage medium accessible via a bus, a computer-readable storage medium accessible via one or more networks and accessible by the device/processor, etc.). Functional facilities comprising these computer-executable instructions may be integrated with and direct the operation of a single multi-purpose programmable digital computing device, a coordinated system of two or more multi-purpose computing devices sharing processing power and jointly carrying out the techniques described herein, a single computing device or coordinated system of computing device (co-located or geographically distributed) dedicated to executing the techniques described herein, one or more Field-Programmable Gate Arrays (FPGAs) for carrying out the techniques described herein, or any other suitable system.

FIG. 4 illustrates one exemplary implementation of a computing device in the form of a computing device 400 that may be used in a system implementing techniques described herein, although others are possible. It should be appreciated that FIG. 4 is intended neither to be a depiction of necessary components for a computing device to operate as a means for receiving and analyzing data from an impedance-EMG needle, or an impedance needle, in accordance with the principles described herein, nor a comprehensive depiction.

Computing device 400 may comprise at least one processor 402, a network adapter 404, and computer-readable storage media 406. Computing device 400 may be, for example, a desktop or laptop personal computer, a personal digital assistant (PDA), a smart mobile phone, a server, a wireless access point or other networking element, or any other suitable computing device. Network adapter 404 may be any suitable hardware and/or software to enable the computing device 400 to communicate wired and/or wirelessly with any other suitable computing device over any suitable computing network. The computing network may include wireless access points, switches, routers, gateways, and/or other networking equipment as well as any suitable wired and/or wireless communication medium or media for exchanging data between two or more computers, including the Internet. Computer-readable media 406 may be adapted to store data to be processed and/or instructions to be executed by processor 402. Processor 402 enables processing of data and execution of instructions. The data and instructions may be stored on the computer-readable storage media 406 and may, for example, enable communication between components of the computing device 400.

The data and instructions stored on computer-readable storage media 406 may comprise computer-executable instructions implementing techniques which operate according to the principles described herein. In the example of FIG. 4, computer-readable storage media 406 stores computer-executable instructions implementing various facilities and storing various information as described above. Computer-readable storage media 406 may store computer-executable instructions for receiving and processing signals from the impedance-EMG needle or the impedance needle, and displaying results on a screen.

While not illustrated in FIG. 4, a computing device may additionally have one or more components and peripherals, including input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Embodiments have been described where the techniques are implemented in circuitry and/or computer-executable instructions. It should be appreciated that some embodiments may be in the form of a method, of which at least one example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Various aspects of the embodiments described above may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," and "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," "having," "containing," "involving," and variations thereof herein, is meant to encompass the items listed thereafter and equivalents thereof as well as additional items.

The word "exemplary" is used herein to mean serving as an example, instance, or illustration. Any embodiment, implementation, process, feature, etc. described herein as exemplary should therefore be understood to be an illustrative example and should not be understood to be a preferred or advantageous example unless otherwise indicated.

Having thus described several aspects of at least one embodiment, it is to be appreciated that various alterations, modifications, and improvements will readily occur to those skilled in the art. Such alterations, modifications, and improvements are intended to be part of this disclosure, and are intended to be within the spirit and scope of the principles described herein. Accordingly, the foregoing description and drawings are by way of example only.

An impedance-EMG needle may be embodied in different configurations. Example configurations may include any combination or combinations of configurations (1) through (18) and (117) as described below.

(1) An impedance-EMG needle configured to be inserted into tissue, the impedance-EMG needle comprising: a shaft; at least one EMG electrode, disposed on the shaft, configured to measure active electrical properties of the tissue; and a plurality of impedance electrodes, disposed on the shaft, configured to measure passive electrical properties of the tissue.

(2) The impedance-EMG needle of configuration (1), wherein the plurality of impedance electrodes are configured as ring electrodes about the shaft of the impedance-EMG needle.

(3) The impedance-EMG needle of configuration (1), wherein the plurality of impedance electrodes are configured as point electrodes on the shaft of the impedance-EMG needle.

(4) The impedance-EMG needle of configuration (1), wherein the plurality of impedance electrodes are configured as open rings on the shaft of the impedance-EMG needle.

(5) The impedance-EMG needle of configuration (1), further comprising an electrochemical biosensor disposed on the shaft of the impedance-EMG needle.

(6) The impedance-EMG needle of configuration (1), wherein the impedance-EMG needle includes a monopolar EMG design, and wherein: the at least one EMG electrode comprises an active EMG electrode disposed at a distal end of the shaft of the impedance-EMG needle; the plurality of impedance electrode are disposed along the shaft of the impedance-EMG needle.

(7) The impedance-EMG needle of configuration (6), wherein the active EMG electrode is electrically connected to a reference EMG electrode disposed on a surface of the tissue.

(8) The impedance-EMG needle of configuration (1), wherein the plurality of impedance electrodes comprises at least four impedance electrodes.

(9) The impedance-EMG needle of configuration (1), wherein the plurality of impedance electrodes comprises four ring electrodes disposed along the shaft of the impedance-EMG needle, and wherein: the outer two ring electrodes are current impedance electrodes; and the inner two ring electrodes are voltage impedance electrodes.

(10) The impedance-EMG needle of configuration (9), wherein the distance between the two voltage impedance electrodes is approximately 0.5 mm.

(11) The impedance-EMG needle of configuration (9), wherein the distance between one of the two current impedance electrodes and an adjacent voltage impedance electrode is approximately 1 mm.

(12) The impedance-EMG needle of configuration (9), wherein the four ring electrodes have a width of approximately 1 mm.

(13) The impedance-EMG needle of configuration (1), wherein a length of the shaft is between approximately 25 mm and 40 mm.

(14) The impedance-EMG needle of configuration (1), wherein the impedance-EMG needle includes a concentric EMG design, wherein the at least one EMG electrode comprises: a reference EMG electrode disposed as an outer layer of the shaft; and an active EMG electrode disposed inside the shaft.

(15) The impedance-EMG needle of configuration (14), further comprising an insulation layer between the active EMG electrode and the reference EMG electrode.

(16) The impedance-EMG needle of configuration (1), wherein a tip of the needle has a sharp or beveled shape.

(17) The impedance-EMG needle of configuration (1), wherein the impedance-EMG needle is configured to be inserted into the tissue to perform in vivo measurements.

(18) The impedance-EMG needle of configuration (1), further comprising insulation disposed on an outer layer of the shaft.

A system for assessing neuromuscular disease of tissue may be embodied in different configurations. Example configurations may include any combination or combinations of configurations (19) through (38) and (118) as described below.

(19) A system for assessing neuromuscular disease of tissue, the system comprising: an impedance-EMG needle configured to be inserted into tissue, the impedance-EMG needle comprising: a shaft; at least one EMG electrode, disposed on the shaft, configured to measure active electrical properties of the tissue; and a plurality of impedance electrodes, disposed on the shaft, configured to measure passive electrical properties of the tissue; and at least one computing device configured to receive and analyze at least one signal from the impedance-EMG needle.

(20) The system of configuration (19), wherein the plurality of impedance electrodes are configured as ring electrodes about the shaft of the impedance-EMG needle.

(21) The system of configuration (19), wherein the plurality of impedance electrodes are configured as point electrodes on the shaft of the impedance-EMG needle.

(22) The system of configuration (19), wherein the plurality of impedance electrodes are configured as open rings on the shaft of the impedance-EMG needle.

(23) The system of configuration (19), further comprising an electrochemical biosensor disposed on the shaft of the impedance-EMG needle.

(24) The system of configuration (19), wherein the impedance-EMG needle includes a monopolar EMG design, and wherein: the at least one EMG electrode comprises an active EMG electrode disposed at a distal end of the shaft of the impedance-EMG needle; the plurality of impedance electrode are disposed along the shaft of the impedance-EMG needle.

(25) The system of configuration (24), wherein the active EMG electrode is electrically connected to a reference EMG electrode disposed on a surface of the tissue.

(26) The system of configuration (19), wherein the plurality of impedance electrodes comprises at least four impedance electrodes.

(27) The system of configuration (19), wherein the plurality of impedance electrodes comprises four ring electrodes disposed along the shaft of the impedance-EMG needle, and wherein: the outer two ring electrodes are current impedance electrodes; and the inner two ring electrodes are voltage impedance electrodes.

(28) The system of configuration (27), wherein the distance between the two voltage impedance electrodes is approximately 0.5 mm.

(29) The system of configuration (27), wherein the distance between one of the two current impedance electrodes and an adjacent voltage impedance electrode is approximately 1 mm.

(30) The system of configuration (27), wherein the four ring electrodes have a width of approximately 1 mm.

(31) The system of configuration (19), wherein a length of the shaft is between approximately 25 mm and 40 mm.

(32) The system of configuration (19), wherein the impedance-EMG needle includes a concentric EMG design, wherein the at least one EMG electrode comprises: a reference EMG electrode disposed as an outer layer of the shaft; and an active EMG electrode disposed inside the shaft.

(33) The system of configuration (32), further comprising an insulation layer between the active EMG electrode and the reference EMG electrode.

(34) The system of configuration (19), wherein a tip of the needle has a sharp or beveled shape.

(35) The system of configuration (19), wherein the impedance-EMG needle is configured to be inserted into the tissue to perform in vivo measurements.

(36) The system of configuration (19), further comprising insulation disposed on an outer layer of the shaft.

(37) The system of configuration (19), wherein the at least one computing device is configured to: receive and analyze at least one first signal, comprising first information relating to the active electrical properties of the tissue, from the at least one EMG electrode; and receive and analyze at least one second signal, comprising second information relating to the passive electrical properties of the tissue, from the plurality of impedance electrodes.

(38) The system of configuration (37), further comprising at least one display, and wherein the at least one computing device is configured to display the first information and the second information on the at least one display.

Methods for assessing neuromuscular disease of tissue may include various processes. Example methods may include any combination or combinations of processes (39) through (56) and (119) as described below.

(39) A method for assessing neuromuscular disease of tissue, the method comprising: inserting an impedance-EMG needle into the tissue, the impedance-EMG needle comprising: a shaft; at least one EMG electrode, disposed on the shaft, configured to measure active electrical properties of the tissue; and a plurality of impedance electrodes, disposed on the shaft, configured to measure passive electrical properties of the tissue; and determining, from the active electrical properties and the passive electrical properties, a state of the tissue.

(40) The method of configuration (39), wherein the plurality of impedance electrodes are configured as ring electrodes about the shaft of the impedance-EMG needle.

(41) The method of configuration (39), wherein the plurality of impedance electrodes are configured as point electrodes on the shaft of the impedance-EMG needle.

(42) The method of configuration (39), wherein the plurality of impedance electrodes are configured as open rings on the shaft of the impedance-EMG needle.

(3) The method of configuration (39), further comprising an electrochemical biosensor disposed on the shaft of the impedance-EMG needle.

(44) The method of configuration (39), wherein the impedance-EMG needle includes a monopolar EMG design, and wherein: the at least one EMG electrode comprises an active EMG electrode disposed at a distal end of the shaft of the impedance-EMG needle; the plurality of impedance electrode are disposed along the shaft of the impedance-EMG needle.

(45) The method of configuration (44), wherein the active EMG electrode is electrically connected to a reference EMG electrode disposed on a surface of the tissue.

(46) The method of configuration (39), wherein the plurality of impedance electrodes comprises at least four impedance electrodes.

(47) The method of configuration (39), wherein the plurality of impedance electrodes comprises four ring electrodes disposed along the shaft of the impedance-EMG needle, and wherein: the outer two ring electrodes are current impedance electrodes; and the inner two ring electrodes are voltage impedance electrodes.

(48) The method of configuration (47), wherein the distance between the two voltage impedance electrodes is approximately 0.5 mm.

(49) The method of configuration (47), wherein the distance between one of the two current impedance electrodes and an adjacent voltage impedance electrode is approximately 1 mm.

(50) The method of configuration (47), wherein the four ring electrodes have a width of approximately 1 mm.

(50) The method of configuration (39), wherein a length of the shaft is between approximately 25 mm and 40 mm.

(51) The method of configuration (39), wherein the impedance-EMG needle includes a concentric EMG design, wherein the at least one EMG electrode comprises: a reference EMG electrode disposed as an outer layer of the shaft; and an active EMG electrode disposed inside the shaft.

(52) The method of configuration (52), further comprising an insulation layer between the active EMG electrode and the reference EMG electrode.

(53) The method of configuration (39), wherein a tip of the needle has a sharp or beveled shape.

(54) The method of configuration (39), wherein the impedance-EMG needle is configured to be inserted into the tissue to perform in vivo measurements.

(55) The method of configuration (39), further comprising insulation disposed on an outer layer of the shaft.

An impedance needle may be embodied in different configurations. Example configurations may include any combination or combinations of configurations (57) through (76) as described below.

(57) An impedance needle configured to be inserted into tissue, the impedance needle comprising: a shaft; and a plurality of impedance electrodes, disposed on the shaft, configured to measure passive electrical properties of the tissue.

(58) The impedance needle of configuration (57), wherein the plurality of impedance electrodes are configured as ring electrodes about the shaft of the impedance needle.

(59) The impedance needle of configuration (57), wherein the plurality of impedance electrodes are configured as point electrodes on the shaft of the impedance needle.

(60) The impedance needle of configuration (57), wherein the plurality of impedance electrodes are configured as open rings on the shaft of the impedance needle.

(61) The impedance needle of configuration (57), further comprising an electrochemical biosensor disposed on the shaft of the impedance needle.

(62) The impedance needle of configuration (57), wherein the plurality of impedance electrodes comprises at least four impedance electrodes.

(63) The impedance needle of configuration (57), wherein the plurality of impedance electrodes comprises four ring electrodes disposed along the shaft of the impedance needle, and wherein: the outer two ring electrodes are current impedance electrodes; and the inner two ring electrodes are voltage impedance electrodes.

(64) The impedance needle of configuration (63), wherein the distance between the two voltage impedance electrodes is approximately 0.5 mm.

(65) The impedance needle of configuration (63), wherein the distance between one of the two current impedance electrodes and an adjacent voltage impedance electrode is approximately 1 mm.

(66) The impedance needle of configuration (63), wherein the four ring electrodes have a width of approximately 1 mm.

(67) The impedance needle of configuration (57), wherein a length of the shaft is between approximately 25 mm and 40 mm.

(68) The impedance needle of configuration (57), wherein a tip of the needle has a sharp or beveled shape.

(69) The impedance needle of configuration (57), wherein the impedance needle is configured to be inserted into the tissue to perform in vivo measurements.

(70) The impedance needle of configuration (57), further comprising insulation disposed on an outer layer of the shaft.

(71) The impedance needle of configuration (57), wherein the impedance needle is configured to measure anisotropy of the tissue.

(72) The impedance needle of configuration (57), wherein: the plurality of impedance electrodes comprises four sets of impedance electrodes; each set of impedance electrodes comprises a plurality of point electrodes disposed in a ring around the shaft of the impedance needle; and each set of impedance electrodes is disposed on its own plane, perpendicular to the length of the impedance needle.

(73) The impedance needle of configuration (72), wherein: each set of impedance electrodes comprises 16 point electrodes, such that the plurality of impedance electrodes comprises a total of 64 point electrodes.

(74) The impedance needle of configuration (72), wherein, in each set of impedance electrodes: an electrical current is configured to be applied across a pair of the impedance electrodes; and another pair of impedance electrodes may be configured to measure a voltage.

(75) The impedance needle of configuration (74), wherein, in each set of impedance electrodes: different pairs of impedance electrodes are configured to have the current applied across them, and different pairs of impedance electrodes are configured to measure the voltage, until a circle has been completed.

(76) The impedance needle of configuration (75), wherein the impedance needle is configured to generate data from which an impedance image of the tissue may be reconstructed.

A system for assessing tissue may be embodied in different configurations. Example configurations may include any combination or combinations of configurations (77) through (100) as described below.

(77) A system configured to assess tissue, the system comprising: an impedance needle configured to be inserted into tissue, the impedance needle comprising: a shaft; and a plurality of impedance electrodes, disposed on the shaft, configured to measure passive electrical properties of the tissue; and at least one computing device configured to receive and analyze at least one signal from the impedance-EMG needle.

(78) The system of configuration (77), wherein the plurality of impedance electrodes are configured as ring electrodes about the shaft of the impedance needle.

(79) The system of configuration (77), wherein the plurality of impedance electrodes are configured as point electrodes on the shaft of the impedance needle.

(80) The system of configuration (77), wherein the plurality of impedance electrodes are configured as open rings on the shaft of the impedance needle.

(81) The system of configuration (77), further comprising an electrochemical biosensor disposed on the shaft of the impedance needle.

(82) The system of configuration (77), wherein the plurality of impedance electrodes comprises at least four impedance electrodes.

(83) The system of configuration (77), wherein the plurality of impedance electrodes comprises four ring electrodes disposed along the shaft of the impedance needle, and wherein: the outer two ring electrodes are current impedance electrodes; and the inner two ring electrodes are voltage impedance electrodes.

(84) The system of configuration (83), wherein the distance between the two voltage impedance electrodes is approximately 0.5 mm.

(85) The system of configuration (83), wherein the distance between one of the two current impedance electrodes and an adjacent voltage impedance electrode is approximately 1 mm.

(86) The system of configuration (83), wherein the four ring electrodes have a width of approximately 1 mm.

(87) The system of configuration (77), wherein a length of the shaft is between approximately 25 mm and 40 mm.

(88) The system of configuration (77), wherein a tip of the needle has a sharp or beveled shape.

(89) The system of configuration (77), wherein the impedance needle is configured to be inserted into the tissue to perform in vivo measurements.

(90) The system of configuration (77), further comprising insulation disposed on an outer layer of the shaft.

(91) The system of configuration (77), wherein the impedance needle is configured to measure anisotropy of the tissue.

(92) The system of configuration (77), wherein: the plurality of impedance electrodes comprises four sets of impedance electrodes; each set of impedance electrodes comprises a plurality of point electrodes disposed in a ring around the shaft of the impedance needle; and each set of impedance electrodes is disposed on its own plane, perpendicular to the length of the impedance needle.

(93) The system of configuration (92), wherein: each set of impedance electrodes comprises 16 point electrodes, such that the plurality of impedance electrodes comprises a total of 64 point electrodes.

(94) The system of configuration (92), wherein, in each set of impedance electrodes: an electrical current is configured to be applied across a pair of the impedance electrodes; and another pair of impedance electrodes may be configured to measure a voltage.

(95) The system of configuration (94), wherein, in each set of impedance electrodes: different pairs of impedance electrodes are configured to have the current applied across them, and different pairs of impedance electrodes are configured to measure the voltage, until a circle has been completed.

(96) The system of configuration (95), wherein the impedance needle is configured to generate data from which an impedance image of the tissue may be reconstructed.

(97) The system of configuration (77), wherein the at least one computing device is configured to: receive and analyze at least one signal, comprising information relating to the passive electrical properties of the tissue, from the plurality of impedance electrodes.

(98) The system of configuration (97), further comprising at least one display, and wherein the at least one computing device is configured to display the first information and the second information on the at least one display.

(99) The system of configuration (96), wherein the at least one computing device is configured to reconstruct the impedance image of the tissue.

(100) The system of configuration (99), further comprising at least one display, and wherein the at least one computing device is configured to display the impedance image on the at least one display.

Methods for generating an impedance image of tissue may include various processes. Example methods may include any combination or combinations of processes (101) through (106) as described below.

(101) A method for generating an impedance image of tissue, the method comprising: inserting an impedance needle into the tissue, the impedance needle comprising: a shaft; and a plurality of impedance electrodes, disposed on the shaft, configured to measure passive electrical properties of a volume of tissue surrounding the plurality of impedance electrodes; and reconstructing the impedance image from the passive electrical properties of the tissue measured by the plurality of impedance electrodes.

(102) The method of configuration (101), wherein: the plurality of impedance electrodes comprises four sets of impedance electrodes; each set of impedance electrodes comprises a plurality of point electrodes disposed in a ring around the shaft of the impedance needle; and each set of impedance electrodes is disposed on its own plane, perpendicular to the length of the impedance needle.

(103) The method of configuration (102), wherein: each set of impedance electrodes comprises 16 point electrodes, such that the plurality of impedance electrodes comprises a total of 64 point electrodes.

(104) The method of configuration (102), further comprising, in each set of impedance electrodes: applying an electrical current across a pair of impedance electrodes; and measuring a voltage with another pair of impedance electrodes.

(105) The method of configuration (104), further comprising, in each set of impedance electrodes: applying the current across different pairs of impedance electrodes and measuring the voltage with different pairs of impedance electrodes until a circle has been completed.

(106) The method of configuration (105), further comprising determining a state of the tissue from the reconstructed impedance image.

Methods for assessing tissue may include various processes. Example methods may include any combination or combinations of processes (107) through (116) as described below.

(107) A method for assessing tissue, the method comprising: inserting at least one impedance needle into the tissue, each of the at least one impedance needles comprising: a shaft; and a plurality of impedance electrodes, disposed on the shaft, configured to measure passive electrical properties of the tissue; and determining a state of the tissue from the passive electrical properties measured by the at least one impedance needle.

(108) The method of configuration (107), wherein the at least one impedance needles are inserted into the tissue at an angle with respect to each other, wherein the angle is measured with respect to a transverse direction and a longitudinal direction of fibers of the tissue.

(109) The method of configuration (108), wherein the passive electrical properties are measured with respect to the angle.

(110) The method of configuration (109), further comprising: inserting the at least one impedance needle a plurality of times to measure the passive electrical properties with respect to different angles, wherein the state of the tissue is determined from the passive electrical properties measured at the different angles.

(111) The method of configuration (107), wherein: each impedance needle comprises at least two impedance electrodes; the length between each impedance electrode is an inter-electrode distance; and the passive electrical properties are measured by varying the number of inter-electrode distances between the impedance electrodes that are measuring the passive electrical properties.

(112) The method of configuration (111), wherein the state of the tissue is determined from the passive electrical properties measured by varying the number of inter-electrode distances between the impedance electrodes that are measuring the passive electrical properties.

(113) The method of configuration (112), wherein the at least one impedance needles are inserted into the tissue at an angle with respect to each other, wherein the angle is measured with respect to a transverse direction and a longitudinal direction of fibers of the tissue.

(114) The method of configuration (113), wherein the passive electrical properties are additionally measured with respect to the angle.

(115) The method of configuration (114), further comprising: inserting the at least one impedance needle a plurality of times to measure the passive electrical properties with respect to different angles.

(116) The method of configuration (115), wherein the state of the tissue is determined by the passive electrical properties measured at different angles and by varying the number of inter-electrode distances between the impedance electrodes that are measuring the passive electrical properties.

(117) The impedance-EMG needle of configuration (1), wherein the tissue is muscle, and wherein: the at least one EMG electrode is configured to measure active electrical properties of the muscle when the muscle is at rest and when the muscle is contracted; and the plurality of impedance electrodes are configured to measure passive electrical properties of the muscle when the muscle is at rest and when the muscle is contracted.

(118) The system of configuration (19), wherein the tissue is muscle, and wherein: the at least one EMG electrode is configured to measure active electrical properties of the muscle when the muscle is at rest and when the muscle is contracted; and the plurality of impedance electrodes are configured to measure passive electrical properties of the muscle when the muscle is at rest and when the muscle is contracted.

(119) The method of configuration (39), wherein the tissue is muscle, and wherein: the at least one EMG electrode is configured to measure active electrical properties of the muscle when the muscle is at rest and when the muscle is contracted; and the plurality of impedance electrodes are configured to measure passive electrical properties of the muscle when the muscle is at rest and when the muscle is contracted.

What is claimed is:

1. An impedance-EMG needle configured to be inserted into tissue, the impedance-EMG needle comprising:
   an insulative shaft of the impedance-EMG needle;
   an active EMG electrode, disposed at a distal end of the insulative shaft, configured to measure active electrical properties of the tissue;
   a reference EMG electrode disposed on an outer layer of the insulative shaft and extending to the distal end of the insulative shaft;
   a plurality of impedance ring electrodes, wherein the plurality of impedance ring electrodes comprises a plurality of current impedance electrodes and a plurality of voltage impedance electrodes and wherein the plurality of voltage impedance electrodes is disposed between the plurality of current impedance electrodes; and
   wherein the plurality of impedance ring electrodes is configured to measure passive electrical properties of the tissue in response to an electrical current with a frequency comprising 10 kHz to 10 MHz.

2. The impedance-EMG needle of claim 1, wherein the plurality of impedance ring electrodes is configured as point electrodes on the insulative shaft of the impedance-EMG needle.

3. The impedance-EMG needle of claim 1, wherein the electrical current has a frequency comprising 10 kHz to 100 kHz.

4. The impedance-EMG needle of claim 1, wherein the plurality of impedance ring electrodes comprises four ring electrodes disposed along the insulative shaft of the impedance-EMG needle, and wherein:
   an outer two ring electrodes are current impedance electrodes; and an
   inner two ring electrodes are voltage impedance electrodes.

5. The impedance-EMG needle of claim 1, wherein the tissue is muscle, and wherein:
   the active EMG electrode is configured to measure active electrical properties of the muscle when the muscle is at rest and when the muscle is contracted; and
   the plurality of impedance ring electrodes is configured to measure passive electrical properties of the muscle when the muscle is at rest and when the muscle is contracted.

6. The impedance-EMG needle of claim 1, wherein the impedance-EMG needle is further configured to measure a temperature of tissue.

7. The impedance-EMG needle of claim 1, wherein the plurality of impedance ring electrodes is configured to measure passive electrical properties of the tissue with the needle being inserted into tissue.

8. A system for assessing neuromuscular disease of tissue, the system comprising:

an impedance-EMG needle configured to be inserted into tissue, the impedance-EMG needle comprising:

an insulative shaft of the impedance-EMG needle;

an active EMG electrode, disposed at a distal end of the insulative shaft, configured to measure active electrical properties of the tissue;

a plurality of impedance ring electrodes, wherein the plurality of impedance ring electrodes comprises a plurality of current impedance ring electrodes and a plurality of voltage impedance electrodes and wherein the plurality of voltage impedance electrodes is disposed between the plurality of current impedance electrodes; and wherein the plurality of impedance ring electrodes is configured to measure passive electrical properties of the tissue in response to an electrical current with a frequency comprising 10 kHz to 10 MHz; and at least one computing device configured to receive and analyze at least one signal from the impedance-EMG needle.

9. The system of claim 8, wherein the electrical current has a frequency comprising 10 kHz to 100 kHz.

10. The system of claim 8, wherein the impedance-EMG needle includes a concentric EMG design, wherein the active EMG electrode comprises:

a first EMG electrode comprising a reference EMG electrode disposed as an outer layer of the insulative shaft; and a second EMG electrode comprising an active EMG electrode disposed inside the insulative shaft.

11. The system of claim 8, wherein the at least one computing device is configured to: receive and analyze at least one first signal, comprising first information relating to the active electrical properties of the tissue, from the at least one EMG electrode; and receive and analyze at least one second signal, comprising second information relating to the passive electrical properties of the tissue, from the plurality of impedance ring electrodes.

12. The system of claim 11, further comprising at least one display, and wherein the at least one computing device is configured to display the first information and the second information on the at least one display.

13. The system of claim 8, wherein the tissue is muscle, and wherein:

the active EMG electrode is configured to measure active electrical properties of the muscle when the muscle is at rest and when the muscle is contracted; and the plurality of impedance ring electrodes is configured to measure passive electrical properties of the muscle when the muscle is at rest and when the muscle is contracted.

14. The system of claim 8, wherein the impedance-EMG needle is further configured to measure a temperature of tissue.

15. The system of claim 8, wherein the plurality of impedance ring electrodes is configured to measure passive electrical properties of the tissue with the needle being inserted into tissue.

16. A method for assessing neuromuscular disease of tissue, the method comprising:

inserting an impedance-EMG needle into the tissue, the impedance-EMG needle comprising:

an insulative shaft of the impedance-EMG needle;

an active EMG electrode, disposed at a distal end of the insulative shaft, configured to measure active electrical properties of the tissue;

a reference EMG electrode disposed on an outer layer of the insulative shaft and extending to the distal end of the insulative shaft;

a plurality of impedance ring electrodes, wherein the plurality of impedance ring electrodes comprises a plurality of current impedance electrodes and a plurality of voltage impedance electrodes and wherein the plurality of voltage impedance electrodes is disposed between the plurality of current impedance electrodes;

wherein the plurality of impedance ring electrodes is configured to measure passive electrical properties of the tissue in response to an electrical current with a frequency comprising 10 kHz to 10 MHz; and determining, from the active electrical properties and the passive electrical properties, a state of the tissue.

17. The method of claim 16, wherein the electrical current has a frequency comprising 10 kHz to 100 kHz.

18. The method of claim 16, wherein the tissue is muscle, and wherein:

the active EMG electrode is configured to measure active electrical properties of the muscle when the muscle is at rest and when the muscle is contracted; and the plurality of impedance ring electrodes is configured to measure passive electrical properties of the muscle when the muscle is at rest and when the muscle is contracted.

19. The method of claim 16, wherein the impedance-EMG needle is further configured to measure a temperature of tissue.

* * * * *